(12) United States Patent
Hart et al.

(10) Patent No.: US 8,026,341 B2
(45) Date of Patent: Sep. 27, 2011

(54) TRANSFECTION COMPLEXES

(75) Inventors: Stephen Lewis Hart, London (GB); Michele Writer, London (GB)

(73) Assignee: ICH Productions Limited, London (GB)

( * ) Notice: Subject to any disclaimer, the term of this patent is extended or adjusted under 35 U.S.C. 154(b) by 0 days.

(21) Appl. No.: 12/724,588

(22) Filed: Mar. 16, 2010

(65) Prior Publication Data

US 2010/0172930 A1 Jul. 8, 2010

Related U.S. Application Data

(63) Continuation of application No. 11/891,790, filed on Aug. 13, 2007, now Pat. No. 7,704,969, which is a continuation of application No. 10/471,895, filed as application No. PCT/GB02/01215 on Mar. 14, 2002, now Pat. No. 7,256,043.

(30) Foreign Application Priority Data

Mar. 14, 2001 (GB) .................................. 0106315.5

(51) Int. Cl.
*C07K 7/00* (2006.01)
*A61K 48/00* (2006.01)
*C07H 21/04* (2006.01)
(52) U.S. Cl. ......... 530/300; 514/44; 435/455; 536/23.1; 536/24.5
(58) Field of Classification Search ........................ None
See application file for complete search history.

(56) References Cited

U.S. PATENT DOCUMENTS 6,344,436 B1 * 2/2002 Smith et al. .................... 514/2
6,376,248 B1 * 4/2002 Hawley-Nelson et al. ... 435/458

FOREIGN PATENT DOCUMENTS

| EP | 0 819 758 A2 | 1/1998 |
|---|---|---|
| WO | WO 98/54347 A1 | 12/1998 |
| WO | WO 00/25814 A2 | 5/2000 |
| WO | WO 00/62815 A2 | 10/2000 |
| WO | WO 00/75174 A1 | 12/2000 |
| WO | WO 01/08708 A2 | 2/2001 |

OTHER PUBLICATIONS

Almeida et al., "Mouse Egg Integrin 6β1 Functions as a Sperm Receptor", Cell, 81:1095-1104 (1995).
Anderson et al., "Construction and Biological Characterization of an Interleukin-12 Fusion Protein (Flexi-12): Delivery to Acute Myeloid Leukemic Blasts Using Adeno-Associated Virus", Human Gene Therapy, 8:1125-1135 (1997).
Barry et al., "Toward cell-targeting gene therapy vectors: Selection of cell-binding peptides from random peptide-presenting phage libraries", Nature Medicine, 2(3): 299-305 (1996).
Bergelson et al., "Identification of the Integrin VLA-2 as a Receptor for Echovirus 1", Science, 255: 1718-1720 (1992).
Bettinger et al., "Size Reduction of Galactosylated PEI/DNA Complexes Improves Lectin-Mediated Gene Transfer into Hepatocytes", Bioconjugate Chem., 10:558-561 (1999).
Blank et al., "Cell Cycle Versus Density Dependence of Smooth Muscle Alpha Actin Expression in Cultured Rat Aortic Smooth Muscle Cells", The Journal of Cell Biology, 107: 299-306 (1988).
Blattner et al., "The Complete Genome Sequence of *Escherichia coli* K-12", Science, 277: 1453-1462 (1997).
Brunner et al., "Cell cycle dependence of gene transfer by lipoplex, polyplex and recombinant adenovirus", Gene Therapy, 7: 401-407 (2000).
Clements et al., "Identification of a key integrin-binding sequence in VCAM-1 homologous to the LDV active site in fibronectin", Journal of Cell Science, 107: 2127-2135 (1994).
Cotten et al., "Transferrin-polycation-mediated introduction of DNA into human leukemic cells: Stimulation by agents that affect the survival of transfected DNA or modulate transferring receptor levels", Proc. Natl. Acad. Sci. USA, 87: 4033-4037 (1990).
Curiel et al., "Adenovirus enhancement of transferrin-polylysine-mediated gene delivery", Proc. Natl. Acad. Sci. USA, 88: 8850-8854 (1991).
Database EBI (Online), *E. coli*, Database accession No. P77280 (1997).
Farhood et al., "The role of dioleoyl phosphatidylethanolamine in cationic liposome mediated gene transfer", Biochimica et Biophyisca Acta, 1235: 289-295 (1995).
Feero et al., "Selection and use of ligands for receptor-mediated gene delivery to myogenic cells", Gene Therapy, 4: 664-674 (1997).
Ferkol et al., "Gene Transfer into the Airway Epithelium of Animals by Targeting the Polymeric Immunoglobulin Receptor", J. Clin. Invest., 95: 493-502 (1995).
Fernandez et al., "Involvement of β1 integrins in the binding and entry of Trypanosoma cruzi into human macrophages", Eur. J. Immunol. 23: 552-557 (1993).
Feuillet et al., "High gene density is conserved at syntenic loci of small and large grass genomes", Proc. Natl. Acad. Sci. USA, 96: 8265-8270 (1999).
Haberland et al., "Calcium ions as efficient cofactor of polycation-mediated gene transfer", Biochimica et Biophyisca Acta, 1445: 21-30 (1999).
Han et al., "Receptor-Mediated Gene Transfer to Cells of Hepatic Origin by Galactosylated Albumin-Polylysine Complexses", Biol. Pharm. Bull. 22(8): 836-840 (1999).

(Continued)

*Primary Examiner* — Richard Schnizer
(74) *Attorney, Agent, or Firm* — Yankwich & Associates, P.C.; Leon R. Yankwich; Michael R. Wesolowski

(57) ABSTRACT

The invention provides a peptide having at least 3 amino acids comprising an amino acid sequence selected from a) $X^1SM$         [SEQ.ID.NO.: 1]
b) $LX^2HK$        [SEQ.ID.NO.: 2]
c) $PSGX^3ARA$     [SEQ.ID.NO.: 9]
d) $SX^4RSMNF$     [SEQ.ID.NO.: 16]
e) $LX^5HKSMP$     [SEQ.ID.NO.: 18]

in which $X^1$ is a basic amino acid residue, $X^2$ is Q or P, $X^3$ is A or T, $X^4$ is an acidic amino acid residue and $X^5$ is P or Q. The invention further provides non-viral cell-targeting vector complexes and methods associated therewith.

24 Claims, 8 Drawing Sheets

OTHER PUBLICATIONS

Hart et al., "Cell Binding and Internalization by Filamentous Phage Displaying a Cyclic Arg-Gly-Asp-containing Peptide", The Journal of Biological Chemistry, 269(17): 12468-12474 (1994).
Hart et al., "Gene delivery and expression mediated by an integrin-binding peptide", Gene Therapy, 2: 552-554 (1995).
Hart et al., "Integrin-mediated transfection with peptides containing arginine-glycine-aspartic acid domains", Gene Therapy, 4: 1225-1230 (1997).
Hart et al., "Lipid-Mediated Enhancement of Transfection by a Nonviral Integrin-Targeting Vector", Human Gene Therapy, 9: 575-585 (1998).
Healy et al., "Peptide Ligands for Integrin vβ3 Selected from Random Phage Display Libraries", Biochemistry, 34: 3948-3955 (1995).
Hendrix et al., "Evolutionary relationships among diverse bacteriophages and prophages: All the world's a phage", Proc. Natl. Acad. Sci. USA, 96: 2192-2197 (1999).
Hsieh et al., "Novel Nuclear Localization Signal Between the Two DNA-Binding Zinc Fingers in the Human Vitamin D Receptor", Journal of Cellular Biochemistry, 70: 94-109 (1998).
Isberg, R.R., "Discrimination Between Intracellular Uptake and Surface Adhesion of Bacterial Pathogens", Science, 252: 934-938 (1991).
Jost et al., "A novel peptide, THALWHT, for the targeting of human airway epithelia", FEBS Letters, 489: 263-269 (2001).
Kohli et al., "Epitope Mapping of the Major Inner Capsid Protein of Group A Rotavirus Using Peptide Synthesis", Virology, 194: 110-116 (1993).
Koivunen et al., "Selection of Peptides Binding to the 5β1 Integrin from Phage Display Library", The Journal of Biological Chemistry, 268(27): 20205-20210 (1993).
Koivunen et al., "Isolation of a Highly Specific Ligand for the 5β1 Integrin from a Phage Display Library", The Journal of Cell Biology, 124(3): 373-380 (1994).
Koivunen et al., "Phage Libraries Displaying Cyclic Peptides with Different Ring Sizes: Ligand Specificities of the RGD-Directed Integrins", Biotechnology, 13: 265-270 (1994).
Logan et al., "Structure of a major immunogenic site on foot-and-mouth disease virus", Nature, 362: 566-569 (1993).
Lu et al., "Synthetic RGD peptides derived from the adhesive domains of snake-venom proteins: evaluation as inhibitors of platelet aggregation", Biochem. J., 296: 21-24 (1993).
Mahata et al., "Primary Structure and Function of the Catecholamine Release Inhibitory Peptide Catestatin (Chromogranin A344-364): Identification of Amino Acid Residues Crucial for Activity", Molecular Endocrinology, 14(10): 1525-1535 (2000).
Massia et al., "Vascular Endothelial Cell Adhesion and Spreading Promoted by the Peptide REDV of the IIICS Region of Plasma Fibronectin Is Mediated by Integrin 4β1", The Journal of Biological Chemistry, 267(20): 14019-14026 (1992).
Nicklin et al., "Selective Targeting of Gene Transfer to Vascular Endothelial Cells by Use of Peptides Isolated by Phage Display", Circulation, 102: 231-237 (2000).
O'Neil et al., "Identification of Novel Peptide Antagonists for GPIIb/IIIa From a Conformationally Constrained Phage Peptide Library", Proteins: Structure, Function and Genetics, 14: 509-515 (1992).
Park et al., "Assessment of Novel Anti-p185HER-2 Monoclonal Antibodies for Internalization-Dependent Therapies", Hybridoma, 18(6): 487-495 (1999).
Pasqualini et al., "A Pepetide Isolated from Phage Display Libraries Is a Structural and Functional Mimic of an RGD-binding site on Integrins", The Journal of Cell Biology, 130(5): 1189-1196 (1995).
Pasqualini et al., "Tissue targeting with phage peptide libraries", Molecular Pyschiatry, 1: 423 (1996).
Pasqualini et al., "Organ targeting in vivo using phage display peptide libraries", Nature, 380: 364-366 (1996).
Phillips, S.C., "Receptor-mediated DNA Delivery Approaches to Human Gene Therapy", Biologicals, 23: 13-16 (1995).
Pierschbacher et al., "Cell attachment activity of fibronectin can be duplicated by small synthetic fragments of the molecule", Nature, 309: 30-33 (1984).
Reddy et al., "Optimization of Folate-Conjugated Liposomal Vectors for Folate Receptor-Mediated Gene Therapy", Journal of Pharmaceutical Sciences, 88(11): 1112-1118 (1999).
Reddy et al., "Enhanced folate receptor mediated gene therapy using a novel pH-sensitive lipid formulation", Journal of Controlled Release, 64: 27-37 (2000).
Reiman et al., "Recognition of a Bacterial Adhesin by an Integrin: Macrophage CR3,(Mβ2, CD11b/CD18) Binds Filamentous Hemagglutinin of Bordetella pertussis", Cell, 61: 1375-1382 (1990).
Rosenkranz et al., "Receptor-Mediated Endocytosis and Nuclear Transport of a Transfecting DNA Construct", Experimental Cell Research, 199: 323-329 (1992).
Samoylova et al., Elucidation of Muscle-Binding Peptides by Phage Display Screening, Muscle & Nerve, 22: 460-466 (1999).
Schneider et al., "A novel peptide, Plaeidgielty, for the targeting of 9β1-integrins", FEBS Letters, 429: 269-273 (1998).
Staatz et al., "Identification of a Tetrapeptide Recognition Sequence for the 2β1 Integrin in Collagen", The Journal of Biological Chemistry, 266(12): 7363-7367 (1991).
Tseng et al., "Mitosis enhances transgene expression of plasmid delivered by cationic liposomes", Biochimica et Biophyisca Acta, 1445: 53-64 (1999).
Uherek et al., "A Modular DNA Carrier Protein Based on the Structure of Diphtheria Toxin Mediates Target Cell-specific Gene Delivery", The Journal of Biological Chemistry, 273(15): 8835-8841 (1998).
Velucchi et al., "Molecular Requirements of Peptide Structures Binding to the Lipid-A Region of Bacterial Endotoxins", Vaccines, 94: 141-146 (1994).
Verfaillie et al., "Adhesion of Commited Human Hematopoietic Progenitors to Synthetic Peptides From the C-Terminal Heparin-Binding Domain of Fibronectin: Cooperation Between the Integrin 4β1 and the CD44 Adhesion Receptor", Blood, 84(6): 1802-1811 (1994).
Wagner et al., "DNA-Binding Transferrin Conjugates as Functional Gene-Delivery Agents: Synthesis by Linkage of Polylysine or Ethidium Homodimer to the Transferrin Carbohydrate Moiety", Bioconjugate Chem., 2: 226-231 (1991).
Wang et al., "The crystal structure of an N-terminal two-domain fragment of vascular cell adhesion molecule 1 (VCAM-1): A cyclic peptide based on the domain 1 C-D loop can inhibit VCAM-1-4 integrin interaction", Proc. Natl. Acad. Sci. USA, 92: 5714-5718 (1995).
Wang et al., "Influence of Cell Polarity on Retrovirus-Mediated Gene Transfer to Differentiated Human Airway Epithelia", Journal of Virology, 72(12): 9818-9826 (1998).
Wang et al., "Increasing Epithelial Junction Permeability Enhances Gene Transfer to Airway Epithelia In Vivo", Am. J. Respir. Cell Mol. Biol., 22: 129-138 (2000).
Wickham et al., "Integrin vβ5 Selectively Promotes Adenovirus Mediated Cell Membrane Permeabilization", The Journal of Cell Biology, 127(1): 257-264 (1994).
Wilke et al., "Efficacy of a peptide-based gene delivery system depends on mitotic activity", Gene Therapy, 3: 1133-1142(1996).
Wolfert et al., "Atomic force microscopic analysis of the influence of the molecular weight of poly(L)lysine on the size of polyelectrolyte complexes formed with DNA", Gene Therapy, 3: 269-273 (1996).
Wu et al., "Receptor-mediated in Vitro Gene Transformation by a Soluble DNA Carrier System", The Journal of Biological Chemistry, 262(10): 4429-4432 (1987).
Wu et al., "Receptor-mediated Gene Delivery in Vivo", The Journal of Biological Chemistry, 266(22): 14338-14342 (1991).
Yano et al., "Improved Gene Transfer to Neuroblastoma Cells by a Monoclonal Antibody Targeting RET, a Receptor Tyrosine Kinase", Human Gene Therapy, 11: 995-1004 (2000).
Zhang et al., "A transfecting peptide derived from adenovirus fiber protein", Gene Therapy, 6: 171-181 (1999).

* cited by examiner

```
                         SEQUENCE LISTING

<160> NUMBER OF SEQ ID NOS: 44

<210> SEQ ID NO 1
<211> LENGTH: 3
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (1)..(1)
<223> OTHER INFORMATION: X=basic amino acid

<400> SEQUENCE: 1

Xaa Ser Met
1

<210> SEQ ID NO 2
<211> LENGTH: 4
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (2)..(2)
<223> OTHER INFORMATION: X=Q or P

<400> SEQUENCE: 2

Leu Xaa His Lys
1

<210> SEQ ID NO 3
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 3

Pro Ser Gly Ala Ala Arg Ala
1               5

<210> SEQ ID NO 4
<211> LENGTH: 7
<212> TYPE: PRT
```

```
<213> ORGANISM: Artificial Sequence
<220> FEATURE:
<223> OTHER INFORMATION: Targeting peptide, see description

<400> SEQUENCE: 4

Leu Gln His Lys Ser Met Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 5

Leu Pro His Lys Ser Met Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 6

Val Lys Ser Met Val Thr His
1               5

<210> SEQ ID NO 7
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 7

Ser Glu Arg Ser Met Asn Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 8

Val Gly Leu Pro His Lys Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (4)..(4)
<223> OTHER INFORMATION: X=A or T

<400> SEQUENCE: 9

Pro Ser Gly Xaa Ala Arg Ala
1               5

<210> SEQ ID NO 10
```

```
<211> LENGTH: 9
<212> TYPE: PRT
<213> ORGANISM: Artificial Sequence
<220> FEATURE:
<223> OTHER INFORMATION: Targeting peptide, see description

<400> SEQUENCE: 10

Cys Leu Pro His Lys Ser Met Pro Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Targeting peptide, see description

<400> SEQUENCE: 11

Cys Leu Gln His Lys Ser Met Pro Cys
1               5

<210> SEQ ID NO 12
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 12

Lys Lys Lys Lys Lys Lys Lys Lys Lys Lys Lys Lys Lys Lys Lys
1               5                   10                  15

Gly Ala Cys Leu Gln His Lys Ser Met Pro Cys Gly
            20                  25

<210> SEQ ID NO 13
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 13

Lys Lys Lys Lys Lys Lys Lys Lys Lys Lys Lys Lys Lys Lys Lys
1               5                   10                  15

Gly Ala Cys Leu Pro His Lys Ser Met Pro Cys Gly
            20                  25

<210> SEQ ID NO 14
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 14

Lys Lys Lys Lys Lys Lys Lys Lys Lys Lys Lys Lys Lys Lys Lys
1               5                   10                  15

Gly Ala Cys Tyr Lys His Pro Gly Phe Leu Cys Gly
            20                  25

<210> SEQ ID NO 15
<211> LENGTH: 31
<212> TYPE: PRT
<213> ORGANISM: Artificial Sequence
<220> FEATURE:
<223> OTHER INFORMATION: Targeting peptide, see description
<220> FEATURE:
```

```
<221> NAME/KEY: MISC_FEATURE
<222> LOCATION: (17)..(17)
<223> OTHER INFORMATION: X=epsilon-amino hexanoic acid
<220> FEATURE:
<221> NAME/KEY: MISC_FEATURE
<222> LOCATION: (19)..(19)
<223> OTHER INFORMATION: X=epsilon-amino hexanoic acid

<400> SEQUENCE: 15

Lys Lys Lys Lys Lys Lys Lys Lys Lys Lys Lys Lys Lys Lys Lys
1               5                   10                  15

Xaa Ser Xaa Gly Ala Cys Arg Arg Glu Thr Ala Trp Ala Cys Gly
            20                  25                  30

<210> SEQ ID NO 16
<211> LENGTH: 7
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (2)..(2)
<223> OTHER INFORMATION: X=acidic amino acid

<400> SEQUENCE: 16

Ser Xaa Arg Ser Met Asn Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (2)..(2)
<223> OTHER INFORMATION: X=E or Q

<400> SEQUENCE: 17

Ser Xaa Arg Ser Met Asn Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Targeting peptide, see description
<220> FEATURE:
<221> NAME/KEY: MISC_FEATURE
<222> LOCATION: (2)..(2)
<223> OTHER INFORMATION: X=P or Q

<400> SEQUENCE: 18

Leu Xaa His Lys Ser Met Pro
1               5

<210> SEQ ID NO 19
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 19

Tyr Gly Leu Pro His Lys Phe
1               5
```

```
<210> SEQ ID NO 20
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 20

Ser Glu Arg Ser Met Asn Phe
1               5

<210> SEQ ID NO 21
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 21

Tyr Lys His Pro Gly Phe Leu
1               5

<210> SEQ ID NO 22
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 22

Asn Ser Phe Met Glu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 23

Ala Gly Ser Ala Arg Pro Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 24

Pro Leu Ser His Gln Met Lys
1               5

<210> SEQ ID NO 25
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 25

His Pro Pro Met Ser Lys Leu
1               5

<210> SEQ ID NO 26
```

```
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 26

Arg Arg Glu Thr Glu Trp Ala
1               5

<210> SEQ ID NO 27
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 27

Lys Lys Lys Lys Lys Lys Lys Lys Lys Lys Lys Lys Lys Lys Lys Lys
1               5                   10                  15

Gly Ala Cys Ser Glu Arg Ser Met Asn Phe Cys Gly
            20                  25

<210> SEQ ID NO 28
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 28

Lys Lys Lys Lys Lys Lys Lys Lys Lys Lys Lys Lys Lys Lys Lys Lys
1               5                   10                  15

Gly Ala Cys Val Lys Ser Met Val Thr His Cys Gly
            20                  25

<210> SEQ ID NO 29
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 29

Lys Lys Lys Lys Lys Lys Lys Lys Lys Lys Lys Lys Lys Lys Lys Lys
1               5                   10                  15

Gly Ala Cys Pro Ser Gly Ala Ala Arg Ala Cys Gly
            20                  25

<210> SEQ ID NO 30
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 30

Lys Lys Lys Lys Lys Lys Lys Lys Lys Lys Lys Lys Lys Lys Lys Lys
1               5                   10                  15

Gly Ala Cys Tyr Lys His Pro Gly Phe Leu Cys Gly
            20                  25

<210> SEQ ID NO 31
<211> LENGTH: 28
<212> TYPE: PRT
<213> ORGANISM: Artificial Sequence
```

```
<220> FEATURE:
<223> OTHER INFORMATION: Targeting peptide, see description

<400> SEQUENCE: 31

Lys Lys Lys Lys Lys Lys Lys Lys Lys Lys Lys Lys Lys Lys Lys Lys
1               5                   10                  15

Gly Ala Cys Asn Ser Phe Met Glu Ser Arg Cys Gly
            20                  25

<210> SEQ ID NO 32
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 32

Lys Lys Lys Lys Lys Lys Lys Lys Lys Lys Lys Lys Lys Lys Lys Lys
1               5                   10                  15

Gly Ala Cys Ala Gly Ser Ala Arg Pro Ala Cys Gly
            20                  25

<210> SEQ ID NO 33
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 33

Lys Lys Lys Lys Lys Lys Lys Lys Lys Lys Lys Lys Lys Lys Lys Lys
1               5                   10                  15

Gly Ala Cys Pro Leu Ser His Gln Met Lys Cys Gly
            20                  25

<210> SEQ ID NO 34
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 34

Lys Lys Lys Lys Lys Lys Lys Lys Lys Lys Lys Lys Lys Lys Lys Lys
1               5                   10                  15

Gly Ala Cys His Pro Pro Met Ser Lys Leu Cys Gly
            20                  25

<210> SEQ ID NO 35
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 35

Lys Lys Lys Lys Lys Lys Lys Lys Lys Lys Lys Lys Lys Lys Lys Lys
1               5                   10                  15

Gly Ala Cys Arg Arg Glu Thr Glu Trp Ala Cys Gly
            20                  25

<210> SEQ ID NO 36
<211> LENGTH: 7
<212> TYPE: PRT
<213> ORGANISM: Artificial Sequence
```

```
<220> FEATURE:
<223> OTHER INFORMATION: Targeting peptide, see description

<400> SEQUENCE: 36

Ser Gln Arg Ser Met Asn Phe
1               5

<210> SEQ ID NO 37
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 37

Gln Pro Leu Arg His His Gln
1               5

<210> SEQ ID NO 38
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 38

Pro Ser Gly Thr Ala Arg Ala
1               5

<210> SEQ ID NO 39
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 39

Lys Gln Arg Pro Ala Trp Leu
1               5

<210> SEQ ID NO 40
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 40

Ile Pro Met Asn Ala Pro Trp
1               5

<210> SEQ ID NO 41
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 41

Ser Leu Pro Phe Ala Arg Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Targeting peptide, see description
```

```
<400> SEQUENCE: 42

Gly Pro Ala Arg Ile Ser Phe
1               5

<210> SEQ ID NO 43
<211> LENGTH: 7
<212> TYPE: PRT
<213> ORGANISM: Artificial Sequence
<220> FEATURE:
<223> OTHER INFORMATION: Targeting peptide, see description

<400> SEQUENCE: 43

Met Gly Leu Pro Leu Arg Phe
1               5

<210> SEQ ID NO 44
<211> LENGTH: 28
<212> TYPE: PRT
<213> ORGANISM: Artificial Sequence
<220> FEATURE:
<223> OTHER INFORMATION: Targeting peptide, see description

<400> SEQUENCE: 44

Lys Lys Lys Lys Lys Lys Lys Lys Lys Lys Lys Lys Lys Lys Lys Lys
1               5                   10                  15

Gly Ala Cys Tyr Gly Leu Pro His Lys Phe Cys Gly
            20                  25
```

TRANSFECTION COMPLEXES

CROSS-REFERENCE TO RELATED APPLICATIONS

This application is a continuation of U.S. Ser. No. 11/891,790, filed Aug. 13, 2007 now U.S. Pat. No. 7,704,969, in issue, which application is a continuation of U.S. Ser. No. 10/471,895, filed Jan. 30, 2004 (now U.S. Pat. No. 7,256,043), which is a United States national filing under 35 U.S.C. §371 of international (PCT) application No. PCT/GB02/01215, filed Mar. 14, 2002, designating the United States, and claiming priority to GB 01 06 315.5, filed Mar. 14, 2001.

BACKGROUND OF THE INVENTION

The present invention relates to peptides for use in an improved method of transfecting cells.

The term "transfection" is used herein to denote the introduction of a nucleic acid into a cell. The nucleic acid may be of any origin, and the recipient cell may be prokaryotic or eukaryotic.

Gene therapy and gene vaccination are techniques that offer interesting possibilities for the treatment and/or prophylaxis of a variety of conditions, as does anti-sense therapy. Such techniques require the introduction of a DNA of interest into target cells. The ability to transfer sufficient DNA to specific target cells remains one of the main limitations to the development of gene therapy, anti-sense therapy and gene vaccination. Both viral and non-viral DNA delivery systems have been proposed. In some cases RNA is used instead of DNA.

Receptor-mediated gene delivery is a non-viral method of gene transfer that exploits the physiological cellular process, receptor-mediated endocytosis to internalise DNA. Examples include vectors targeted against insulin receptors, see for example, Rosenkranz et al Experimental Cell Research 199, 323-329 (1992), asialoglycoprotein receptors, see for example, Wu & Wu, Journal of Biological Chemistry 262, 4429-4432 (1987), Chowdhury et al Journal of Biological Chemistry 268, 11265-11271 (1993), and transferrin receptors, see for example, Ciriel et al, Proc. Natl. Acad. Sci. USA 88, 8850-8854 (1991). Further examples of vectors include monoclonal antibodies targeting receptors on neuroblastoma cells (Yano et al, 2000), folate conjugated to liposomes (Reddy & Low 2000, Reddy et al. 1999), galactose for targeting liver cells (Han et al. 1999 Bettinger et al. 1999) and asialogylcoprotein, also for liver cells (Wu et al. 1991).

Receptor-mediated non-viral vectors have several advantages over viral vectors. In particular, they lack pathogenicity; they allow targeted gene delivery to specific cell types and they are not restricted in the size of nucleic acid molecules that can be packaged. Gene expression is achieved only if the nucleic acid component of the complex is released intact from the endosome to the cytoplasm and then crosses the nuclear membrane to access the nuclear transcription machinery. However, transfection efficiency is generally poor relative to viral vectors owing to endosomal degradation of the nucleic acid component, failure of the nucleic acid to enter the nucleus and the exclusion of aggregates larger than about 150 nm from clathrin coated vesicles.

Desirable properties of targeting ligands for vectors are that they should bind to cell-surface receptors with high affinity and specificity and mediate efficient vector internalisation. Short peptides have particular advantages as targeting ligands since they are straightforward to synthesise in high purity and, importantly for in vivo use, they have low immunogenic potential.

WO 98/54347 discloses a mixture comprising an integrin-binding component, a polycationic nucleic acid-binding component, and a lipid component, and also discloses a complex comprising
(i) a nucleic acid, especially a nucleic acid encoding a sequence of interest,
(ii) an integrin-binding component,
(iii) a polycationic nucleic acid-binding component, and
(iv) a lipid component.

The complex is primarily an integrin-mediated transfection vector.

Integrins are a super-family of heterodimeric membrane proteins consisting of several different $\alpha$ and $\beta$ subunits. They are important for attachment of cells to the extracellular matrix, cell-cell interactions and signal transduction. Integrin-mediated internalisation proceeds by a phagocytic-like process allowing the internalisation of bacterial cells one to two micrometers in diameter (Isberg, 1991). Targeting of non-viral vectors to integrins, therefore, has the potential to transfect cells in a process that mimics infection of cells by pathogens and avoids the size limitation imposed by clathrin-coated vesicles in receptor-mediated endocytosis.

It is considered that the components described in WO 98/54347 associate electrostatically to form the vector complex, the vector being of the lipopolyplex type. The vector complexes of WO 98/54347 are found to transfect a range of cell lines and primary cell cultures with high efficiency, with integrin specificity and with low toxicity. For example, vascular smooth muscle cells are transfected with 50% efficiency, endothelial cells with 30% efficiency and haemato-poietic cells with 10% efficiency. Furthermore, in vivo transfection of bronchial epithelium of rat lung and pig lung with an efficiency comparable with that of an adenoviral vector has been demonstrated.

Vectors that utilise integrin receptors to mediate gene transfer have the advantage that they target a large number of different types of cells in the body as integrin receptors are relatively widespread. In some circumstances, for example, in in vivo treatment, however, it may be preferable to target recipient cells more specifically.

BRIEF SUMMARY OF THE INVENTION

It is an object of the present invention to provide improved vector complexes with enhanced cell targeting properties. The present invention is based on the development of synthetic targeting non-viral vector complexes that carry a ligand that is more cell-type selective than the ligands of the prior art.

Previous approaches to targeted non-viral vectors have included the use of antibodies to substances involved in cell-cell adhesion. For example, vectors including monoclonal antibodies that target receptors on neuroblastoma cells (Yano et al, 2000) are known. Further examples of targeting systems have proposed galactose for targeting liver cells (Han et al. 1999 Bettinger et al. 1999) and asialogylcoprotein, also for liver cells (Wu et al. 1991). However, such methods have been effective only in limited circumstances. For example, antibodies have broad applicability but they are time-consuming to produce and, by virtue of their size, are not as suitable for in vivo administration to an organism as a small molecule ligand. Furthermore, the methods previously described do not allow targeting to a cell type for which a ligand is not yet available.

In the development of effective targeting vectors it is useful for several different target-binding ligands to be available. Effective targeted transfection requires not only good targeting but also effective transfer of the vector DNA to the nucleus of the target cell. Even if a ligand is effective in targeting and binding to a target cell, effective gene transfection does not always occur. The reasons for that are, at present, not clear. Accordingly, there remains a degree of unpredictability regarding whether a ligand that binds effectively to a target cell will also bring about effective transfection. It is therefore desirable to have available a "pool" of ligands for any particular cell surface receptor from which an effective transfection ligand may be selected. Such selection may take place by means of a gene transfer assay using, for example, a reporter gene, or by any other suitable means.

The invention is based on the identification of specific peptide sequences that bind to human airway epithelial (HAE) cells. The identified families of HAE cell surface receptor binding component peptide motifs mediate specific binding to HAE cells.

DETAILED DESCRIPTION OF THE INVENTION

The present invention provides peptide having consisting of or comprising an amino acid sequence selected from a) $X^1$SM; [SEQ.ID.NO.: 1]

b) $LX^2$HK; [SEQ.ID.NO.: 2]

c) $PSGX^3$ARA; [SEQ.ID.NO.: 9]

d) $SX^4$RSMNF; [SEQ.ID.NO.: 16]
and e) $LX^5$HKSMP, [SEQ.ID.NO.: 18]

in which $X^1$ is a basic amino acid residue, $X^2$ is Q or P, $X^3$ is A or T, $X^4$ is an acidic amino acid residue and $X^5$ is P or Q.

Preferably, the peptide of the invention consists of or comprises an amino acid sequence selected from a) $X^1$SM; [SEQ.ID.NO.: 1]

b) $LX^2$HK; [SEQ.ID.NO.: 2]
and c) PSGAARA, [SEQ.ID.NO.: 3]

in which $X^1$ is a basic amino acid residue and $X^2$ is Q or P.

Preferably $X^1$ is K or R. Preferably $X^2$ is P. Preferably $X^3$ is A. Preferably $X^4$ is E or Q [SEQ.ID.No.::17]. More preferably $X^4$ is E. Preferably $X^5$ is P.

Preferably, a peptide of the invention comprises a sequence selected from LQHKSMP [SEQ.ID.NO.:4], LPHKSMP [SEQ.ID.NO.:5], VKSMVTH [SEQ.ID.NO.:6], SERSMNF [SEQ.ID.NO.:7], VGLPHKF [SEQ.ID.NO.:8], YGLPHKF [SEQ.ID.NO.:19], PSGAARA [SEQ.ID.NO.:3], SQRSMNF [SEQ.ID.NO.:36] and PSGTARA [SEQ.ID.NO.:38]. Most preferably, the peptide comprises a sequence selected from LQHKSMP [SEQ.ID.NO.:4], and LPHKSMP [SEQ.ID.NO.:5].

A peptide of the invention may be up to 20 amino acids in length, or may be longer. A peptide of the invention generally has at least 5 amino acids but may have perhaps fewer. Generally, a peptide of the invention has any number of amino acids from 6 to 20 inclusive. The peptide may have 6, 7, 8, 9, 10, 11, 12, 13, 14, 15, 16, 17, 18, 19 or 20 amino acids. Generally, it is preferred for a peptide of the invention to have 15 amino acids or fewer. For example, a peptide of the invention may have 12 amino acids or fewer. Preferably a peptide of the invention according to the invention has 10 amino acids or fewer. Generally, it is preferred for a peptide of the invention to have 5 or more amino acids. For example, a peptide of the invention may have 6 or more amino acids. For example a peptide of the invention has 7 amino acids. In the case of a peptide comprising amino acid sequence c) above, the minimum size is 7 amino acids.

Preferably, a peptide of the invention is such that $X^1$ is K or R or $X^2$ is Q or P.

A peptide of the invention may comprise a cyclic region. Preferably, the motif of the invention is flanked by two or more cysteine residues that are capable of forming one or more disulphide bond(s). For example, a peptide of the invention may be "peptide P'" (CLPHKSMPC [SEQ.ID.NO.:10]) or "peptide Q'" (CLQHKSMPC [SEQ.ID.NO.:11]).

The peptides of the invention find use in HAE cell targeted non-viral transfection vector complexes. They are also useful in targeted viral transfection vectors.

The peptide is preferably linked to a polycationic nucleic acid binding component. The polycationic nucleic acid binding component may be any polycationic molecule suitable for binding a nucleic acid.

For example, it may be polyethylenimine. Polyethylenimine (PEI) is a non-toxic, cross linked cationic polymer with gene delivery potential (*Proc. Natl. Acad. Sci.,* 1995, 92, 7297-7301). For example, the peptide may be linked to the PEI structure via a disulphide bridge using methods known in the art (for example, *Gene Therapy,* 1999, 6, 138-145). Polyethylenimine is obtainable from Fluka (800 kDa) or from Sigma (50 kDa) or alternatively pre-diluted for transfection purposes from PolyPlus-transfection (Illkirch, France). Typically, PEI is most efficient when in a 9 fold excess over DNA (the excess ratio being calculated as PEI nitrogen:DNA phosphate) and at pH 5-8. Such parameters may optimised in a manner familiar to the person skilled in the art.

Another example of a nucleic acid-binding polycationic molecule is an oligopeptide comprising one or more cationic amino acids. Such a oligopeptide may, for example, be an oligo-lysine molecule having from 5 to 25 lysine moieties, preferably having from 10 to 20 lysine moieties, for example 16 lysine moieties, an oligo-histidine molecule, or an oligo-arginine molecule or a combined oligomer comprising any combination of histidine, arginine and lysine residues and having a total of from 5 to 25 residues, preferably having from 10 to 20 residues, for example 16 residues.

The peptide may be attached to the polycationic nucleic acid binding component via a spacer.

A spacer element is generally a peptide, that is to say, it comprises amino acid residues. The amino acids may be naturally occurring or non-naturally occurring. They may have L- or D-configuration. A spacer may have two or more amino acids. It may, for example, comprise three or more amino acids, for example, four or more, for example, five or more, for example, up to ten amino acids or more. The amino acids may be the same or different, but the use of multiple lysine residues (or other cationic amino acids suitable for use in the polycationic nucleic acid-binding component of a vector complex) should be avoided in the spacer as oligolysine sequences have activity as a polycationic nucleic acid-binding component of a vector complex of the present invention.

The spacer may be, for example, the dipeptide glycine-glycine (GG) or glycine-alanine (GA). Generally it is preferable that the spacer is longer and/or more hydrophobic than the dipeptide spacers GG and GA.

The spacer may be more hydrophobic than the dipeptides GG and GA. For example, amino acids that are more hydrophobic than glycine and alanine may be used. Examples of hydrophobic amino acids are well known and include ε-amino hexanoic acid.

A spacer may be either longer or more hydrophobic than the dipeptides GG and GA, or it may be both longer and more hydrophobic. An example of the latter type of spacer is XSXGA, wherein S=serine, G=glycine, A=alanine and X=ε-amino hexanoic acid. This spacer is highly hydrophobic.

The invention further provides a peptide derivative of formula A-B-C wherein

A is a polycationic nucleic acid-binding component,
B is a spacer element, and
C is a peptide as described above.

Polycationic nucleic acid-binding component A may be any polycationic nucleic acid-binding component as described above. Spacer element B may be any of the spacer elements described above.

The invention further provides a non-viral transfection complex comprising:
(i) a nucleic acid,
(ii) a lipid component,
(iii) a polycationic nucleic acid-binding component, and
(iv) a cell surface receptor binding component, comprising a peptide as described above.

The cell surface receptor binding component may have the features described above in relation to the peptides of the invention.

The cell surface receptor binding component peptides were identified by selection from a peptide library of random 7-mers (peptides having seven amino acid residues) and random 12-mers (peptides having twelve amino acid residues) displayed on filamentous phage particles. Results obtained using the random 7-mer library were better than those using the random 12-mer peptide library. The reasons for the difference in performance of the seven and twelve amino acid library are not known at present. It is possible that the larger amino acid insert in the phage coat protein reduces the viability of the phage and/or that the additional protein synthesis requirement places too great a burden on the E. coli bacteria. Alternatively, or in addition, impurities in or defects of the 12-mer library may have adversely affected the outcome of the experiments with that library. It appears, however, that smaller peptides, for example heptameric peptides are preferred. Accordingly, the peptide of the invention preferably has 4 to 11 amino acids, more preferably 4 to 10 amino acids, for example 7 amino acids.

The 7-mer library used was a C7C library (i.e. random 7-mer peptides flanked by cysteine residues) obtained from New England Biolabs Inc. The 12-mer library used was also obtained from New England Biolabs Inc.

As indicated above, the HAE cell surface receptor binding peptides of the invention were identified by selection from a phage display library comprising random peptide sequences seven residues in length flanked by cysteine residues to allow cyclisation. Such selection procedures are generally known. According to such procedures, suspensions of phage are incubated with target cells. Unbound phage are then washed away and, subsequently, bound phage are extracted either by washing the remaining cells with a low pH buffer or by lysing the cells. E. coli are then infected with released phage and a preparation of first round phage is obtained. The cycle is performed repeatedly, for example three times and, in order to enrich for targeting phage, the stringency conditions may be increased in the later rounds of selection, for example by increasing the number of wash steps, introducing a low pH wash prior to elution and preselecting with wells coated with medium blocker.

Following selection by successive rounds of phage amplification, it has been found that phage with high affinity for HAE cells may be selected further by whole cell ELISA using plated HAE cells.

Following incubation of the phage with the HAE cells, the cells are washed and retained phage may then be detected by immunostaining. Cell specificity is assessed by comparing phage binding to target cells with phage binding to the wells on which the cells were plated and with phage binding to NIH 3T3 fibroblast control cells.

Using the whole cell ELISA (Enzyme-Linked ImmunoSorbent Assay) assay described above, high affinity and high specificity binding peptides were identified. The cells to which high affinity phage were bound were lysed to release the bound phage particles. The phage DNA was isolated and sequenced.

The amino acid sequences of clones obtained from cell lysis eluted C7C phage in a first experiment are shown in Table 1a.

TABLE 1a

| Sequence | Clone frequency | SEQ.ID |
|---|---|---|
| LQHKSMP | 3 | 4 |
| LPHKSMP | 1 | 5 |
| YGLPHKF | 1 | 19 |
| SERSMNF | 3 | 7 |
| VKSMVTH | 2 | 6 |
| PSGAARA | 2 | 3 |

The amino acid sequences of clones obtained from cell lysis eluted C7C phage in a second experiment are shown in Table 1b.

TABLE 1b

| Sequence | Clone Frequency | SEQ.ID.NO. |
|---|---|---|
| SERSMNF | 18 | 7 |
| YGLPHKF | 12 | 19 |
| PSGAARA | 9 | 3 |
| LQHKSMP | 3 | 4 |
| VKSMVTH | 3 | 6 |
| SQRSMNF | 2 | 36 |
| QPLRHHQ | 2 | 37 |
| LPHKSMP | 1 | 5 |
| PSGTARA | 1 | 38 |
| KQRPAWL | 1 | 39 |
| IPMNAPW | 1 | 40 |
| SLPFARN | 1 | 41 |
| GPARISF | 1 | 42 |
| MGLPLRF | 1 | 43 |

The 56 sequenced clones from the third round of panning of HAEo– in the second experiment were represented by the 14 sequences shown in Table 1b, with some sequences being represented by multiple phage clones. The sequences shown were each flanked by two cysteine residues in the phage and are thus constrained in a loop formation by disulphide bonds between them. For the avoidance of doubt, all of the sequences in Tables 1a and 1b form part of the present invention An analysis of the motifs found in the positive clone amino acid sequences of Table 1a (the first experiment) is shown in Table 2a.

TABLE 2a

| Motif | Sequence | SEQ. ID. | Clone frequency | Motif frequency |
|---|---|---|---|---|
| KSM/RSM | LQHKSMP | 4 | 3 | 9 |
|  | LPHKSMP | 5 | 1 |  |
|  | VKSMVTH | 6 | 2 |  |
|  | SERSMNF | 7 | 3 |  |
| LXHK | LQHKSMP | 4 | 3 | 5 |
|  | LPHKSMP | 5 | 1 |  |
|  | YGLPHKF | 19 | 1 |  |
| LXHKSMP (SEQ ID NO: 18) | LQHKSMP | 4 | 3 | 4 |
|  | LPHKSMP | 5 | 1 |  |
| PSGAARA* | PSGAARA | 3 | 2 | 2 |

*PSGAARA (SEQ ID NO: 3) is not a motif, but a repeated clone in the first experiment not containing any motifs already identified.

An analysis of the motifs found in the positive clone amino acid sequences of Table 1b (the second experiment) is shown in Table 2b.

TABLE 2b

| Motif | Sequence | SEQ. ID. | Clone frequency | Motif frequency |
|---|---|---|---|---|
| KSM/RSM | SERSMNF | 7 | 18 | 27 |
|  | SQRSMNF | 36 | 2 |  |
|  | VKSMVTH | 6 | 3 |  |
|  | LQHKSMP | 4 | 3 |  |
|  | LPHKSMP | 5 | 1 |  |
| SXRSMNF (SEQ ID NO: 16) | SERSMNF | 7 | 18 | 20 |
|  | SQRSMNF | 36 | 2 |  |
| LXHK (SEQ ID NO: 12) | LQHKSMP | 4 | 3 | 16 |
|  | LPHKSMP | 5 | 1 |  |
|  | YGLPHKF | 19 | 12 |  |
| PSGXAPA (SEQ ID NO: 9) | PSGAARA | 3 | 9 | 10 |
|  | PSGTARA | 38 | 1 |  |
| LXHKSMP (SEQ ID NO: 18) | LPHKSMP | 5 | 3 | 4 |
|  | LQHKSMP | 4 | 1 |  |

The sequences found in the first experiment (Table 1a) were compared and ranked for their binding strength by ELISA using a range of phage titres (Table 3). In Table 3, the sequences are ranked in order of binding affinity to HAE cells. It was found that the sequence LPHKSMP (SEQ ID NO: 5) ("Peptide P") had the highest binding affinity.

TABLE 3

| Sequence | SEQ. ID | Clone frequency | Motifs |
|---|---|---|---|
| LPHKSMP | 5 | 1 | LXHK (SEQ ID NO: 2), LXHKSMP (SEQ ID NO: 18), KSM |
| LQHKSMP | 4 | 3 | LXHK (SEQ ID NO: 2), LXHKSMP (SEQ ID NO: 18), KSM |
| YGLPHKF | 19 | 1 | LXHK (SEQ ID NO: 2) |
| VKSMVTH | 6 | 2 | KSM |
| PSGAARA | 3 | 2 | PSGAARA (SEQ ID NO: 9) |
| SERSMNF | 7 | 3 | RSM |

From the Tables it may be seen that the motifs KSM/RSM and LXHK were present in several of the clones. This strongly suggests that those motifs are important for HAE cell surface binding. It is at present not known to which HAE receptor(s) the sequences bind. The various motifs may target the same receptor or they may target different receptors.

Good binding indicates a high affinity interaction and/or the binding of a cell surface receptor molecule present in high numbers on the cell surface. The LPHK version of the LXHK motif provides better binding than the LQHK version and the KSM version of the XSM motif provides better binding than the RSM version. The LXHK motif and the KSM motif are frequently found together. This may be due to a cooperative effect, possibly due to the motifs binding to two cell surface receptor molecules.

Although the peptide sequences of the invention were identified using HAE cells, their utility is not limited to use with HAE cells. The receptors to which the peptides bind may be expressed in other cell types. Cell types with which peptides of the invention may be used may be identified by any suitable screening procedure.

The transfection properties the vector complexes of the invention were investigated in HAE cell transfection experiments as described below.

Non-viral transfection vector complexes incorporating the identified sequences were prepared. Peptides were synthesised using standard solid phase synthetic chemistry and a sixteen-lysine tail was added. The most frequently occurring peptides were chosen for synthesis, with peptide LPHKSMP chosen because it contains three motifs. Each peptide was assigned a single letter name. The peptides chosen for synthesis are shown in Table 4.

TABLE 4

| Peptide | Sequence | SEQ. ID. | Clone frequency | Motifs |
|---|---|---|---|---|
| E | SERSMNF | 7 | 18 | RSM, SXRSMNF (SEQ ID NO: 16) |
| Y | YGLPHKF | 19 | 12 | LXHK (SEQ ID NO: 2) |
| G | PSGAARA | 3 | 9 | PSGXARA (SEQ ID NO: 9) |
| V | VKSMVTH | 6 | 3 | KSM |
| Q | LQHKSMP | 4 | 3 | LXHK (SEQ ID NO: 2), LXHKSMP (SEQ ID NO: 18), KSM |
| P | LPHKSMP | 5 | 1 | LXHK (SEQ ID NO: 2), LXHKSMP (SEQ ID NO: 18), KSM |

(Where X = any amino acid)

Luciferase reporter gene DNA was used as the transfection DNA. Transfection complexes were made by mixing the components in the order 1) lipid, then 2) peptide and, finally 3) DNA, followed by dilution. The vector complex suspension was applied to HAE cells and control cells. Vector complexes incorporating peptide Q ([K]$_{16}$-GACLQHKSMPCG [SEQ.ID.NO.:12]) and vector complexes incorporating peptide P ([K]$_{16}$-GACLPHKSMPCG [SEQ.ID.NO.:13]) were synthesised and compared with vector complexes incorporating peptide S ([K]$_{16}$-GACYKHPGFLCG] [SEQ.ID.NO.:14]) which is a control peptide having the same amino acid constituents as peptide P but in a randomised order (the "scrambled control"), Peptide 12 ([K]$_{16}$-XSXGACRRETAWACG [SEQ.ID.NO.:15]), a targeting peptide known to bind to alpha 5 beta 1 integrins and Peptide K ([K]$_{16}$) a DNA binding moiety with no targeting ligand attached.

Transfections of HAE cells and 3T3 cells were performed in 96 well plates containing 20,000 cells plated 24 hours earlier. In the transfection vector complex, peptide to DNA charge ratios (+/−) were used at 1.5:1, 3:1 and 7:1. At physiological pH, DNA carries negative charge and the polycationic-nucleic acid binding component carries positive charge. The "charge ratio" is accordingly the ratio of the charges of the two components in the complex. The lipid component was maintained at a constant proportion, by weight, relative to DNA of 0.75:1. The results of the transfection experiments are shown in FIG. 3.

At a 7:1 charge ratio, the transfection efficiency of vector complexes containing peptide P was five-fold higher than the next best peptide, peptide 12 at a 3:1 charge ratio. Peptide P was 150-fold better than peptide S (the scrambled control) at the charge ratio of 7:1 indicating that the transfection efficiency was receptor specific. Vector complexes containing peptide P were almost nine-fold more efficient those containing peptide K, again indicating receptor specificity. The fact that vector complexes containing peptide K performed better in the assay than vector complexes containing peptide S suggests that steric hindrance by the scrambled motif in peptide S may play a role.

Despite the similar HAE cell surface binding properties of peptide P and peptide Q (See FIG. 2), peptide P performed significantly better than peptide Q in the transfection assay. This result suggests that binding properties alone are not sufficient to achieve high efficiency of transfection.

The HAE cell surface receptor binding peptide component for use in the vector complex of the invention may be synthesised using standard solid phase peptide synthesis methods.

The identity of the molecules bound by the peptides used in transfections was explored by carrying out a BLAST search (Tables 5a and 5b). Homologies were found to several molecules of interest which may bind molecules present on the surface of epithelial cells in the lung. Pathogen peptides with homology with the peptides of the invention are shown in Table 5a, whilst cell adhesion molecules with homology with the peptides of the invention are shown in Table 5b.

TABLE 5a

| Peptide | Homology | Protein | Pathogen | Receptor |
|---|---|---|---|---|
| LPHKSMP/ LQHKSMP | LHKSM | Glycoprotein B | Human herpesvirus | Cell surface heparan sulphate |
| SXRSMNF | SDRSMN | Capsid binding protein VP2 | Human rhinovirus | ICAM-1 or LDL receptor family |
| YGLPHKF | YGLPHK | Unknown | Legionella pneumophila | Unknown epithelial cell receptors |
| VKSMVTH | VKSMITQ | Adhesin P1 | Mycoplasma Pneumoniae | Cell surface sialoglycoproteins |

TABLE 5b

| Peptide | Homology | Protein | Species | Receptor |
|---------|----------|---------|---------|----------|
| SXRSMNF | SERSMN | Selectin | Rat | Cell surface glycoproteins |
|  | ERSMDF | Laminin, alpha 5 | Human | Extracellular matrix components including integrins |
| LXHKSMP | LPHKNM | Epithelial caderin (ovumorulin) | Mouse/ rabbit | Dimerises, also binds integrin a-E, b-7 |

Epithelial cadherin is a molecule which is involved in cell-cell adhesion and forms complexes with β-catenin. Human herpesvirus glycoprotein B binds cell surface heparan sulphate proteoglycans. Selectin binds cell surface glycoproteins. Laminin, alpha 5 is a basement membrane protein found in epithelium. The capsid binding protein VP2 of the rhinovirus binds ICAM-1 or the LDL receptor family of molecules in the upper respiratory tract. P-glycoprotein is a molecular pump molecule which is localised in the cell membrane, and coagulation factor XII has been shown to bind cytokeratins on epithelial cells.

In so far as any motif or any peptide of the invention occurs in a naturally-occurring protein, the peptides of invention do not include such a naturally-occurring full-length protein. Generally, the peptides of the invention are 100 or fewer amino acids in length; preferably the peptides of the invention are 50 or fewer amino acids in length. Typically, they are of sizes described above.

The peptides of the invention finds utility in the study of conditions involving the pathogens and the cell adhesion molecules given in Tables 4a and 4b. They are also useful in the development of treatments for those conditions.

The nucleic acid component may be obtained from natural sources, or may be produced recombinantly or by chemical synthesis. It may be modified, for example, to comprise a molecule having a specific function, for example, a nuclear targeting molecule. The nucleic acid may be DNA or RNA. DNA may be single stranded or double stranded. The nucleic acid may be suitable for use in gene therapy, in gene vaccination or in anti-sense therapy. The nucleic acid may be or may relate to a gene that is the target for particular gene therapy or may be a molecule that can function as a gene vaccine or as an anti-sense therapeutic agent. The nucleic acid may be or correspond to a complete coding sequence or may be part of a coding sequence.

Alternatively, the nucleic acid may encode a protein that is commercially useful, for example industrially or scientifically useful, for example an enzyme; that is pharmaceutically useful, for example, a protein that can be used therapeutically or prophylactically as a medicament or vaccine; or that is diagnostically useful, for example, an antigen for use in an ELISA. Host cells capable of producing commercially useful proteins are sometimes called "cell factories".

Appropriate transcriptional and translational control elements are generally provided. For gene therapy, the nucleic acid component is generally presented in the form of a nucleic acid insert in a plasmid or vector. In some cases, however, it is not necessary to incorporate the nucleic acid component in a vector in order to achieve expression. For example, gene vaccination and anti-sense therapy can be achieved using a naked nucleic acid.

The nucleic acid is generally DNA but RNA may be used in some cases, for example, in cancer vaccination. The nucleic acid component may be referred to below as the plasmid component or component "D".

As indicated above, the polycationic nucleic acid-binding component is any polycation that is capable of binding to DNA or RNA. The polycation may have any number of cationic monomers provided the ability to bind to DNA or RNA is retained. For example, from 3 to 100 cationic monomers may be present, for example, from 10 to 20, for example from 14 to 18, especially about 16. An oligolysine is particularly preferred, for example, having from 10 to 20 lysine residues, for example, from 13 to 19, for example, from 14 to 18, for example, from 15 to 17 residues, especially 16 residues i.e. $[K]_{16}$, "K" denoting lysine.

A further preferred cationic polymer is polyethylenimine (*Proc. Natl. Acad. Sci.*, 1995, 92, 7297-7301).

The polycationic DNA-binding or RNA-binding component may advantageously be linked or otherwise attached to the cell surface receptor-binding component. A combined cell surface receptor-binding component/polycationic DNA-binding or RNA-binding component may be referred to below as component "I". For example, a polycationic DNA-binding or RNA-binding component may be chemically bonded to a cell surface receptor-binding compo-nent, for example, by a peptide bond in the case of an oligolysine. The polycationic component may be linked at any position of the cell surface receptor-binding component. Preferred combinations of cell surface receptor-binding component and polycationic DNA-binding or RNA-binding component are an oligolysine, especially $[K]_{16}$, linked via a peptide bond to a peptide, for example, a peptide as described above. A further preferred combination of cell surface receptor-binding component and polycationic DNA-binding or RNA-binding component are a polyethylenimine linked via a covalent link to a peptide, for example, a peptide as described above. For example such a covalent link may be a disulphide bridge or a succinimidyl bridge.

The lipid component may be or may form a cationic liposome. The lipid component may be or may comprise one or more lipids selected from cationic lipids and lipids having membrane destabilising or fusogenic properties, especially a combination of a cationic lipid and a lipid that has membrane destabilising properties.

A preferred lipid component ("L") is or comprises the neutral lipid dioleyl phosphatidylethanolamine, referred to herein as "DOPE". DOPE has membrane destabilising properties sometimes referred to as "fusogenic" properties (Farhood et al. 1995). Other lipids, for example, neutral lipids, having membrane destabilising properties, especially membrane destabilising properties like those of DOPE may be used instead of or as well as DOPE.

Other phospholipids having at least one long chain alkyl group, for example, di(long alkyl chain)phospholipids may be used. The phospholipid may comprise a phosphatidyl group, for example, a phosphatidylalkanolamine group, for example, a phosphatidyl-ethanolamine group.

A further preferred lipid component is or comprises the cationic lipid N-[1-(2,3-dioleyloxy)propyl]-N,N,N-trimethylammonium chloride, referred to herein as "DOTMA". DOTMA has cationic properties. Other cationic lipids may be used in addition to or as an alternative to DOTMA, in particular cationic lipids having similar properties to those of DOTMA. Such lipids are, for example, quaternary ammonium salts substituted by three short chain alkyl groups, and one long chain alkyl group. The short chain alkyl groups may be the same or different, and may be selected from methyl and ethyl groups. At least one and up to three of the short chain alkyl group may be a methyl group. The long alkyl chain group may have a straight or branched chain, for example, a di(long chain alkyl)alkyl group.

Another preferred lipid component is or comprises the lipid 2,3-dioleyloxy-N-[2-(spermidinecarboxamido)ethyl]-N,N-dimethyl-1-propanaminiumtrifluoridoacetate, referred to herein as "DOSPA". Analogous lipids may be used in addition to or as an alternative to DOSPA, in particular lipids having similar properties to those of DOSPA. Such lipids have, for example, different short chain alkyl groups from those in DOSPA.

A preferred lipid component comprises DOPE and one or more other lipid components, for example, as described above. Especially preferred is a lipid component that comprises a mixture of DOPE and DOTMA. Such mixtures form cationic liposomes. An equimolar mixture of DOPE and DOTMA is found to be particularly effective. Such a mixture is known generically as "lipofectin" and is available commercially under the name "Lipofectin". The term "lipofectin" is used herein generically to denote an equimolar mixture of DOPE and DOTMA. Other mixtures of lipids that are cationic liposomes having similar properties to lipofectin may be used. Lipofectin is particularly useful as it is effective in all cell types tested.

A further preferred lipid component comprises a mixture of DOPE and DOSPA. Such mixtures also form cationic liposomes. A mixture of DOPE and DOSPA in a ratio by weight 3:1 DOSPA:DOPE is particularly effective. Such a mixture, in membrane filtered water, is available commercially under the name "Lipofectamine". Mixtures comprising DOPE, DOTMA and DOSPA may be used, for example, mixtures of lipofectin and lipofectamine.

Other cationic lipids are available commercially, for example, DOTAP (Boehringer-Mannheim) and lipids in the Tfx range (Promega). DOTAP is N-[1-(2,3-diolyloxy)propyl]-N,N,N-tri-methylammonium methylsulphate. The Tfx reagents are mixtures of a synthetic cationic lipid [N,N,N',N'-tetramethyl-N,N'-bis(2-hydroxyethyl)-2,3-di(oleoyloxy)-1,4-butanediammonium iodide and DOPE. All the reagents contain the same amount of the cationic lipid component but contain different molar amounts of the fusogneic lipid, DOPE.

However, lipofectin and lipofectamine appear to be markedly more effective as the lipid component in LID vector complexes of the present invention than are DOTPA and Tfx agents.

The effectiveness of a putative cell surface receptor-binding component, polycationic DNA-binding or RNA-binding component, or of lipid component or of any combination thereof may be determined readily using the methods described herein.

The efficiency of transfection using a transfection complex as described above as transfection vector is influenced by the ratio lipid component:cell surface receptor-binding component:DNA or RNA. For any chosen combination of components for any particular type of cell to be transfected, the optimal ratios can be determined simply by admixing the components in different ratios and measuring the transfection rate for that cell type, for example, as described herein.

Lipofectin and lipofectamine appear to be particularly effective in enhancing transfection in the system described above. Lipofectin has the advantage that only very small amounts are required. Any side effects that may occur are therefore minimised. A suitable weight ratio between the lipid and the DNA components has been found to be 0.75:1. For any given transfection experiment, this ratio may be optimised using methods known in the art.

Cells that may be transfected by a transfection vector complex incorporating a peptide of the invention include, for example, endothelial or epithelial cells, for example, cells of the any part of the airway epithelium, including bronchial and lung epithelium, and the corneal endothelium. The airway epithelium is an important target for gene therapy for cystic fibrosis and asthma.

A transfection vector complex as described above may be produced by admixing components (i), (ii), (iii) and (iv).

Although the components may be admixed in any order, it is generally preferable that the lipid component is not added last. In the case where there is a combined cell surface receptor-binding component/polycationic DNA-binding or RNA-binding component it is generally preferable to combine the components in the following order: lipid component; combined cell surface receptor-binding/polycationic DNA-binding or RNA-binding component; DNA or RNA component, for example, in the order: lipofectin, oligolysine-peptide component, DNA or RNA component.

A transfection mixture comprising a cell surface receptor-binding component, a polycationic nucleic acid-binding component, and a lipid component may be used to produce a nucleic acid-containing transfection vector complex as described above by the incorporation of a nucleic acid with the mixture, for example, by admixture. Alternatively, the transfection mixture may be used for the production of a vector complex which comprises, instead of the nucleic acid component, any other component that is capable of binding to the polycationic nucleic-acid binding component, for example, a protein.

The individual components of a transfection mixture of the invention are each as described above in relation to the transfection vector complex. The preferred components, preferred combinations of components, preferred ratios of components and preferred order of mixing, both with regard to the mixture and to the production of a vector complex, are as described above in relation to the transfection vector complex.

A transfection mixture preferably comprises an equimolar mixture of DOPE and DOTMA (lipofectin) as the lipid component and an oligolysine-peptide especially a $[K]_{16}$-peptide as a combined cell surface receptor-binding component/nucleic acid-binding component. The preferred molar ratio lipofectine:oligolysine-peptide is 0.75:4.

The invention further provides a non-viral transfection complex comprising:
(i) a nucleic acid,
(iii) a polycationic nucleic acid-binding component, and
(iv) a cell surface receptor binding component, comprising a peptide as described above.

The cell surface receptor binding component may have the features described above in relation to the peptides of the invention. The nucleic acid component and the polycationic nucleic acid-binding component may be as described above in relation to the non-viral transfection complex comprising (i), (ii), (iii) and (iv).

The effectiveness of a putative cell surface receptor-binding component and polycationic DNA-binding or RNA-binding component may be determined readily using the methods described herein.

The efficiency of transfection using a transfection complex as described above as transfection vector is influenced by the ratio of cell surface receptor-binding component:polycationic nucleic acid-binding component:DNA or RNA. For any chosen combination of components for any particular type of cell to be transfected, the optimal ratios can be determined simply by admixing the components in different ratios and measuring the transfection rate for that cell type, for example, as described herein.

Cells that may be transfected by a transfection vector complex incorporating a peptide of the invention include, for example, endothelial or epithelial cells, for example, cells of any part of the airway epithelium, including bronchial and lung epithelium, and the corneal endothelium. The airway epithelium is an important target for gene therapy for cystic fibrosis and asthma.

A transfection vector complex as described above may be produced by admixing components (i), (iii) and (iv).

Although the components may be admixed in any order, it is generally preferable to combine the components in the following order: combined cell surface receptor-binding/polycationic DNA-binding or RNA-binding component; DNA or RNA component, for example, in the order: polyethylenimine-peptide component; DNA or RNA component.

A transfection mixture comprising a cell surface receptor-binding component and a polycationic nucleic acid-binding component may be used to produce a nucleic acid-containing transfection vector complex as described above by the incorporation of a nucleic acid with the mixture, for example, by admixture. Alternatively, the transfection mixture may be used for the production of a vector complex which comprises, instead of the nucleic acid component, any other component that is capable of binding to the polycationic nucleic-acid binding component, for example, a protein.

The individual components of a transfection mixture of the invention are each as described above in relation to the transfection vector complex. The preferred components, preferred combinations of components, preferred ratios of components and preferred order of mixing, both with regard to the mixture and to the production of a vector complex, are as described above in relation to the transfection vector complex.

The present invention also provides a process for expressing a nucleic acid in host cells, which comprises contacting the host cells in vitro or in vivo with a receptor-targeted vector complex of the invention comprising the nucleic acid and then culturing the host cells under conditions that enable the cells to express the nucleic acid.

The present invention further provides a process for the production of a protein in host cells, which comprises contacting the host cells in vitro or in vivo with a receptor-targeted vector complex of the invention that comprises a nucleic acid that encodes the protein, allowing the cells to express the protein, and obtaining the protein. The protein may be obtained either from the host cell or from the culture medium.

The present invention further provides a method of transfecting cells comprising subjecting the cells to a vector complex according to the invention.

The invention further provides cells, transfected with a nucleic acid by a method according to the invention, and also the progeny of such cells.

The present invention further provides a disease model for use in testing candidate pharmaceutical agent, which comprises cells transfected by a method according to the invention with a nucleic acid suitable for creating the disease model.

The present invention also provides a pharmaceutical composition which comprises a receptor-targeted vector complex of the invention comprising a nucleic acid in admixture or conjunction with a pharmaceutically suitable carrier. The composition may be a vaccine.

The present invention also provides a method for the treatment or prophylaxis of a condition caused in a human or in a non-human animal by a defect and/or a deficiency in a gene, which comprises administering to the human or to the non-human animal a receptor-targeted vector complex of the invention comprising a nucleic acid suitable for correcting the defect or deficiency.

The present invention also provides a method for therapeutic or prophylactic immunisation of a human or of a non-human animal, which comprises administering to the human or to the non-human animal a receptor-targeted vector complex of the invention comprising an appropriate nucleic acid.

The present invention also provides a method of anti-sense therapy of a human or of a non-human animal, comprising anti-sense DNA administering to the human or to the non-human animal a receptor-targeted vector complex of the invention comprising the anti-sense nucleic acid.

The present invention also provides the use of a receptor-targeted vector complex of the invention comprising a nucleic acid for the manufacture of a medicament for the prophylaxis of a condition caused in a human or in a non-human animal by a defect and/or a deficiency in a gene, for therapeutic or prophylactic immunisation of a human or of a non-human animal, or for anti-sense therapy of a human or of a non-human animal.

A non-human animal is, for example, a mammal, bird or fish, and is particularly a commercially reared animal.

The nucleic acid, either DNA or RNA, in the vector complex is appropriate for the intended use, for example, for gene therapy, gene vaccination, or anti-sense therapy. The DNA or RNA and hence the vector complex is administered in an amount effective for the intended purpose.

The treatments and uses described above may be carried out by administering the respective vector complex, agent or medicament in an appropriate manner, for example, administration may be topical, for example, in the case of airway epithelia.

In a further embodiment, the present invention provides a kit comprising a receptor-targeted vector complex of the invention comprising a nucleic acid.

The present invention also provides a kit that comprises the following items: (a) a cell surface receptor-binding component; (b) a polycationic nucleic acid-binding component, and (c) a lipid component. Such a kit may further comprise (d) a nucleic acid. Such a nucleic acid may be single-stranded or double stranded and may be a plasmid or an artificial chromosome. The nucleic acid component may be provided by a vector complex suitable for the expression of the nucleic acid, the vector complex being either empty or comprising the nucleic acid. For in vitro purposes, the nucleic acid may be a reporter gene. For in vivo treatment purposes, the nucleic acid may comprise DNA appropriate for the correction or supplementation being carried out. Such DNA may be a gene, including any suitable control elements, or it may be a nucleic acid with homologous recombination sequences. It has been found that peptide/DNA/lipid/polycationic nucleic acid-binding component complexes are especially stable in salt free buffer (for example in water, or 5% dextrose).

The present invention also provides a kit that comprises the following items: (a) a cell surface receptor-binding component; and (b) a polycationic nucleic acid-binding component. Such a kit may further comprise (d) a nucleic acid. Such a nucleic acid may be single-stranded or double stranded and may be a plasmid or an artificial chromosome. The nucleic acid component may be provided by a vector complex suitable for the expression of the nucleic acid, the vector complex being either empty or comprising the nucleic acid. The nucleic acid component may be provided by a vector complex suitable for the expression of the nucleic acid, the vector complex being either empty or comprising the nucleic acid. For in vitro purposes, the nucleic acid may be a reporter gene. For in vivo treatment purposes, the nucleic acid may comprise DNA appropriate for the correction or supplementation being carried out. Such DNA may be a gene, including any suitable control elements, or it may be a nucleic acid with homologous recombination sequences. It has been found that peptide/DNA/polycationic nucleic acid-binding component complexes are especially stable in salt free buffer (for example in water, or 5% dextrose).

The components (a) to (d) kit are, for example, as described above in relation to a cell surface receptor-targeted transfection vector complex or a mixture as described above.

A kit generally comprises instructions, which preferably indicate the preferred ratios of the components and the preferred order of use or admixing of the components, for example, as described above. A kit may be used for gene therapy, gene vaccination or anti-sense therapy. Alternatively, it may be used for transfecting a host cell with a nucleic acid encoding a commercially useful protein i.e. to produce a so-called "cell factory".

In a kit of the invention the components including the preferred components are, for example, as described above in relation to a vector complex of the present invention.

The polycationic nucleic acid binding component is preferably an oligolysine, as described above. The lipid component is preferably capable of forming a cationic liposome, and preferably is or comprises DOPE and/or DOTMA, for example, an equimolar mixture thereof, or is or comprises DOSPA, for example, a mixture of DOPE and DOSPA, for example in the weight ratio DOPE:DOSPA of 1:3. The rations between the components are preferably as described above, as is the order of mixing of the components.

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, HIV, HCV and herpes simplex virus. Targets for anti-sense therapy are also known. Further targets for gene therapy and anti-sense therapy are being proposed as knowledge of the genetic basis of disease increases, as are further targets for gene vaccination. The present invention enhances the transfection efficiency and hence the effectiveness of the treatment.

Vector complexes of the invention may be effective for intracellular transport of very large DNA molecules, for example, DNA larger than 125 kb, which is particularly difficult using conventional vectors. This enables the introduction of artificial chromosomes into cells.

Transfection of the airways, for example, the bronchial epithelium demonstrates utility for gene therapy of, for example, respiratory diseases, such as cystic fibrosis, emphysema, asthma, pulmonory fibrosis, pulmonary hypertension and lung cancer.

Cystic fibrosis (CF) is the most common monogenic disorder in the Caucasian population. Morbidity is mainly associated with lung disease. CF is caused by mutations in the gene encoding the cystic fibrosis transmembrane conductance regulator protein (CFTR), a cell membrane channel that mediates secretion of chloride ions. Correction of this defect in the bronchial cells by CFTR gene transfer will correct the biochemical transport defect and, hence, the lung disease. Clinical trials so far have generated encouraging data but highlighted the need for more efficient, non-toxic vectors.

The enhanced levels of transfection make the method of the invention particularly suitable for the production of host cells capable of producing a desired protein, so-called "cell factories". For long-term production, it is desirable that the introduced nucleic acid is incorporated in the genome of the host cell, or otherwise stably maintained. That can be readily ascertained. As indicated above, the range of proteins produced in this way is large, including enzymes for scientific and industrial use, proteins for use in therapy and prophylaxis, immunogens for use in vaccines and antigens for use in diagnosis.

Accordingly, the present invention provides a method of testing drugs in a tissue model for a disease, wherein the tissue model comprises transgenic cells obtained by transfecting cells with a nucleic acid by contacting the cell with a receptor-targeted vector complex of the invention comprising a nucleic acid.

The present invention is especially useful with a receptor targeted vector complex that is capable of high efficiency transfection. In a preferred embodiment, the vector complex comprises four modular elements; an oligolysine, especially $[K]_{16}$, DNA-binding or RNA-binding element; a high affinity cell surface receptor-binding peptide, for example, a peptide described herein; a DNA or RNA sequence, optionally in a plasmid, and optionally regulated by a viral promoter and an enhancing element; the cationic liposome DOTMA/DOPE (lipofectin). The combination of oligolysine-peptide/DNA or RNA complex with the cationic liposome formulation DOTMA/DOPE is a potent combination. Alternatively a DOPE/DOSPA formulation may be used instead of or in addition to a DOTMA/DOPE formulation. The optimisation of variables associated with complex formation and the mode of transfection by LID vector complexes has been demonstrated.

The most important variables in the formation of optimal LID transfection complexes appear to be the ratio of the three components and their order of mixing.

The invention further provides a method for identifying a cell surface receptor binding ligand for use in a non-viral transfection vector complex comprising the steps:
 a) selecting phage from a phage peptide library according to their binding affinity to cells of interest by bringing the phage into contact with the cells of interest and washing away non-binding phage and then extracting bound phage particles,
 b) repeating step (a) if necessary, and preferably
 c) selecting from the phage obtained in steps a) and b) those phage which bind to the cell of interest with high affinity using a whole cell ELISA.

Preferably, the stringency of the wash in step a) is increased after the first round of selection by washing at low pH by washing multiple times.

BRIEF DESCRIPTION OF THE DRAWINGS

The following non-limiting Examples illustrate the present invention. The Examples refer to the accompanying drawings, in which.

EXAMPLES

Materials & Methods

Example 1

Peptide Library

The peptide library used in this study, C7C, was obtained from New England Biolabs Inc. Phage growth, titration and amplification procedures were performed as described in the manufacturer's handbook. The library consisted of random peptide sequences seven residues in length and flanked by cystine residues to allow cyclisation by oxidation in air. The library is likely to contain at least $1 \times 10^9$ different amino acid sequences.

Selection of Phage from the Library

HAE cells were grown to confluence in 24-well plates. The HAE cells used were 1HAEo− cells obtained as a gift from Dr. Dieter Gruenert of the University of California, San Francisco (now of the University of Vermont). Cells were washed twice in Tris-buffered saline, pH 7.4 (TBS) before blocking cells with 2 ml 2% Marvel, 5% bovine serum albumin (BSA)-TBS per well for 30 minutes at 4° C. The blocker was removed and $2 \times 10^{11}$ phage were added in 1 ml of 2% Marvel, 5% BAS-TBS. The phage were allowed to bind for 2 hours with shaking at 4° C. before washing five items with 2% BSA-TBS and 5 minutes shaking at 4° C. followed by another five washes with 2% BSA-TBS for a few seconds only. Phage were eluted by the addition of 400 μl 76 mM citrate buffer pH 2.5 to the wells for 10 minutes with shaking at 4° C. The eluate was removed and neutralised with 600 μl 1M Tris buffer pH 7.5 and retained as the eluted fraction. The remaining cells were lysed with 1 ml 30 mM Tris buffer pH 8.0, 1 mM EDTA for 1 hour on ice. The cells were scraped from the plate, the eluate transferred to a microcentrifuge tube, and vortexed briefly. That eluate was retained as the cell-associated fraction.

Figure 1:
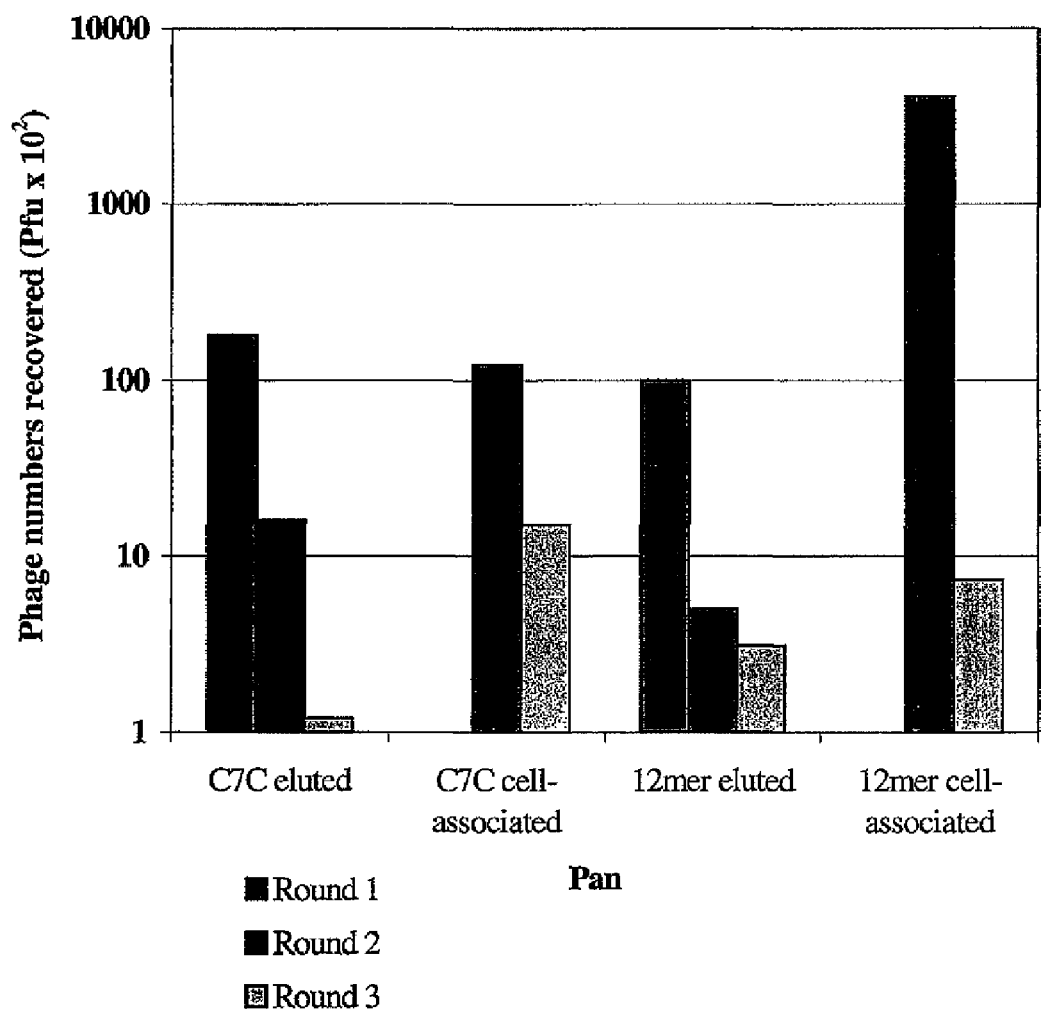
FIG. 1 shows the enhancement of phage binding to HAE cells in successive rounds of selection for the C7C library and the 12 mer peptide library starting materials.

The above described process was repeated three times. In the second and third rounds, the stringency of selection was increased by introduction of preselection steps to remove phage that bind to the plastic or to components in the medium and by increasing the number of washes following phage binding. The number of phage present in each eluate (in plaque forming units, PFU) is shown in FIG. 1.

Whole Cell HAE Cell Binding ELISA

Figure 2:
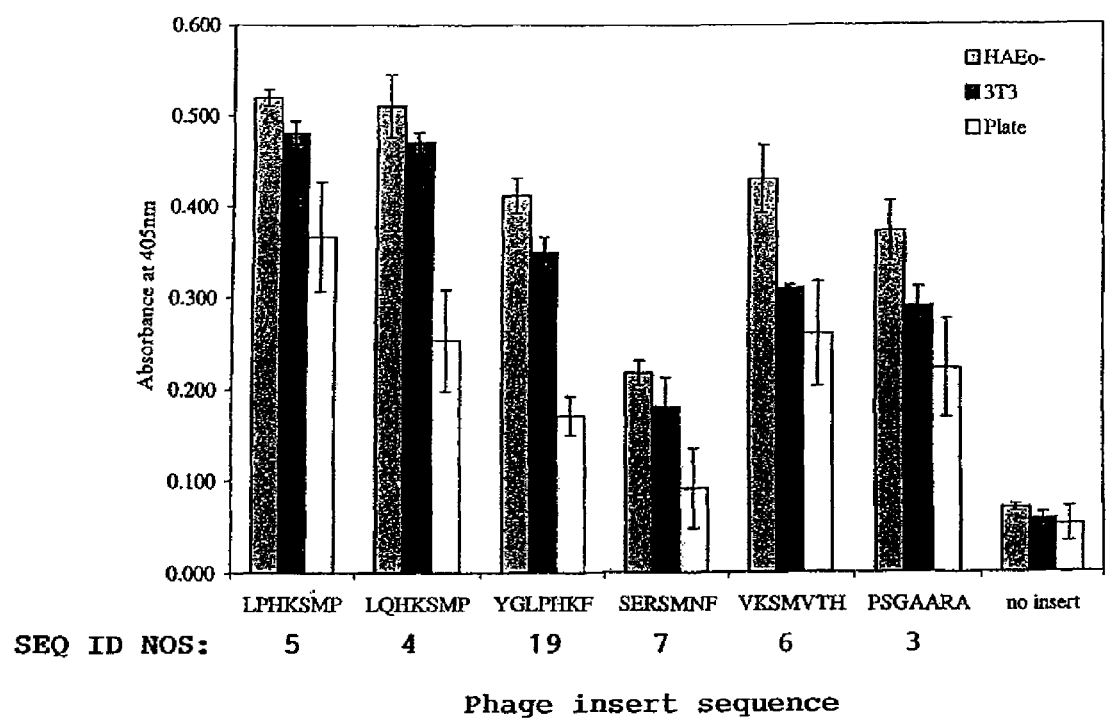
FIG. 2 shows the binding specificity of individual phage clones in a whole cell ELISA assay. Binding affinity to HAE cells, to 3T3 control cells and to the ELISA plate are shown.

Binding of phage to tissue cultured HAE cells was investigated by whole cell ELISA. Approx. $8 \times 10^4$ HAE cells in 100 ml Hanks Balanced Salts Solution (HBSS) were added to each well of a 96 well plate and incubated at 37° C. until cells had adhered. The cells were washed gently in HBSS before blocking by the addition of 0.5% BSA in HBSS for 30 mins. $1 \times 10^{10}$ phage particles in blocker solution were added to each well and allowed to bind at room temperature for 40 minutes. Unbound phage were removed by washing twice with HBSS, and bound phage were fixed to the cells by incubation in 3.7% paraformaldehyde for 10 mins. Cells were washed in PBS and incubated in blocking buffer for 45 mins, followed by three washes in PBS. Bound phage were detected by the addition of horseradish peroxidase (HRP)-conjugated anti-M13 antibody diluted 1:5000 in blocking buffer for 1 hour, before washing three times in PBS and developing the ELISA with 2,2'-azino-bis(3-ethylbenzthiazoline 6-sulfonic acid) (ABTS) substrate solution and reading the absorbance on a plate-reading spectrophotometer at 405 nm. The experiment was repeated using 3T3 cells and using empty wells and the comparison of binding affinities enabled the identification of phage that bound selectively to HAE cells. The results for selected peptides are shown in FIG. 2.

Peptide-encoding DNA of 12 phage clones that displayed high HAE cell avidity and specificity were sequenced and the peptide sequence deduced. The sequences deduced are shown in table 1. Three major peptide motifs, KSM/RSM, LXHK (SEQ ID NO: 2) and LXHKSMP (SEQ ID NO: 18) were identified amongst the 12 sequences and one sequence, PSGAARA (SEQ ID NO: 3) that contained none of the other three motifs. The sequences were compared and ranked for their binding strength by ELISA using a range of phage titres (table 3). It was found that the sequence LPHKSMP (SEQ ID NO: 5) (peptide P) had the highest binding affinity. This sequence and the closely related peptide LQHKSMP (SEQ ID NO: 4) (peptide Q) and a control, scrambled version of peptide P were selected for transfection experiments.

Peptide Synthesis

The following oligolysine-peptides were prepared for transfection experiments:

```
Peptide P:
[K]16-GACLPHKSMPCG - binds to HAE cells

Peptide Q:
[K]16-GACLQHKSMPCG - binds to HAE cells

Peptide S:
[K]16-GACYKHPGFLCG - non-binding control

Peptide 12:
[K]16-XSXGACRRETAWACG - binds to alpha 5 beta 1
integrins (X = ε-amino hexanoic acid)

K16:
DNA binding moiety, no targeting ligand.
```

The oligolysine-peptides were synthesised using standard solid phase oligopeptide synthesis methods.

Transfection Experiments

Figure 3:
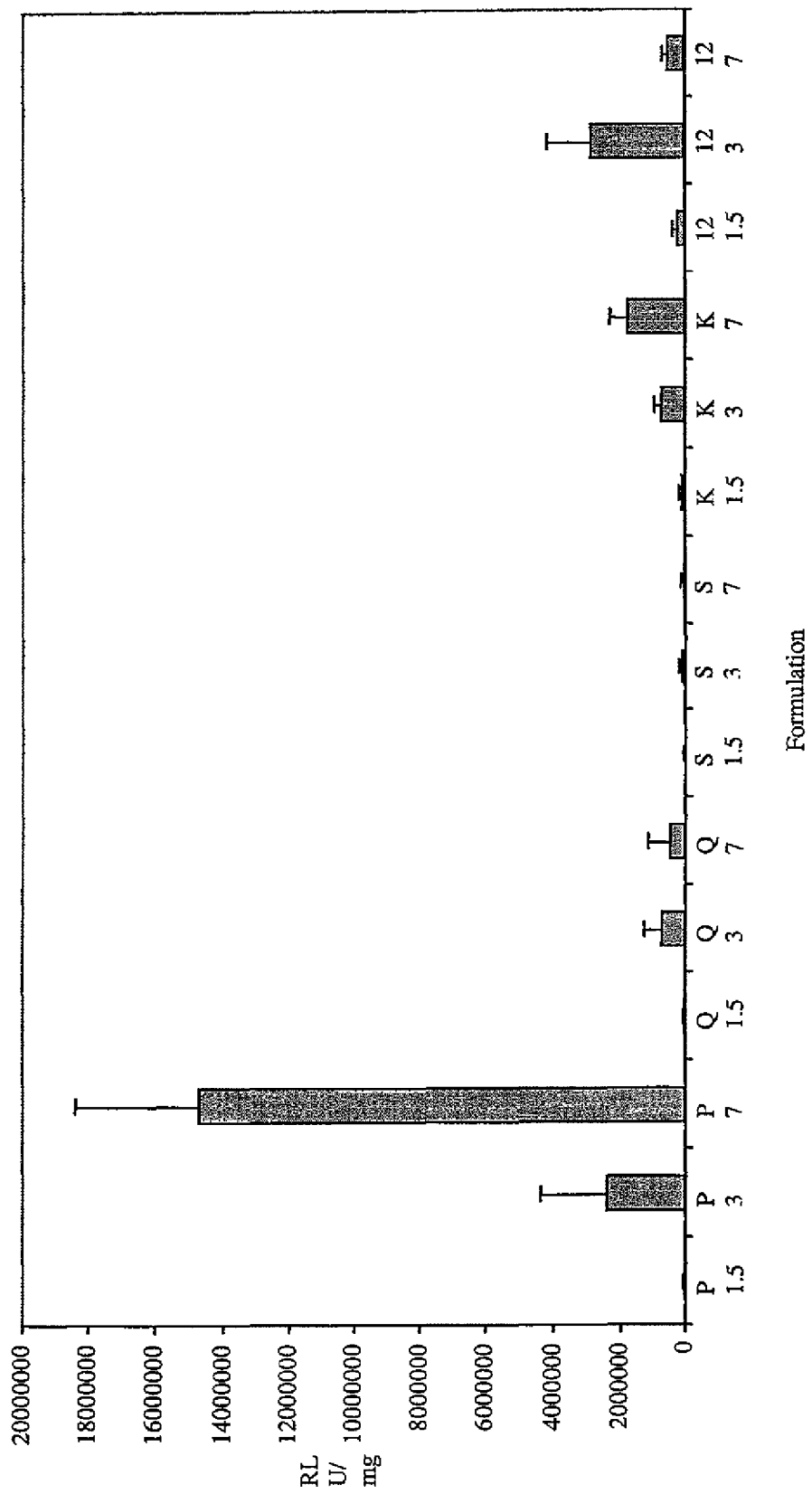
FIG. 3 shows the relative efficiency of transfection of HAE cells achieved by transfection complexes according to the invention.

Peptides identified from phage that displayed desirable cell binding characteristics were synthesised using standard solid-phase peptide synthetic chemistry and a sixteen-lysine tail was attached using standard synthesis methods. Control peptide (S), consisted of the same amino acid constituents as the targeting peptide P but in a randomised order, was synthesised for incorporation into lipopolyplex formulations. Transfections of HAE and 3T3 cells were performed in 96 well plated containing 20,000 cells plated 24 h earlier. In the transfection complex, peptide to DNA charge ratios (+/−) were used at 1.5:1, 3:1 and 7:1. The lipid component was maintained at a constant proportion, by weight, relative to DNA of 0.75:1. Prior to making transfection complexes the lipid component was diluted to a concentration of 15 µg per ml, the peptide was prepared at 0.1 mg/ml and the DNA was at 20 µg per ml. All dilutions were performed with OptiMEM reduced serum tissue culture medium (Life Technologies). Transfection complexes were made by mixing of components in the order 1) lipid then 2) peptide and finally 3) DNA, then diluted with OptiMEM to a concentration relative to the DNA component of 0.25 µg DNA per 200 µl which volume was added to each well. Each group was performed in replicates of six. The vector complex suspension was then applied to cells within 5 minutes of preparation. Transfection incubations were performed at 37° C. for 4 h. Luciferase reporter gene assays in cell free extracts were performed after 48 h incubation using a kit from Promega according to the manufacturer's protocol. Light units were standardised to the protein concentration within each extract. The results of the transfection experiments are shown in FIG. 3.

At a 7:1 charge ratio the transfection efficiency of complexes containing peptide P was five fold-higher than the next best peptide, peptide 12 at a 3:1 ratio. Peptide P was more than 150-fold better than Peptide S at the charge ratio of 7:1 indicating that the transfection efficiency was receptor specific. Complexes containing peptide P were almost nine-fold higher than $K_{16}$, again indicating receptor specificity. This result also suggests that peptide S is less than a tenth as good in transfection complexes as peptide $K_{16}$. This may be explained by steric hindrance by the scrambled motif in peptide S.

The difference in transfection performance between peptides P and Q was unexpected as peptide Q (LQHKSMP) (SEQ ID NO: 4) varies from peptide P by a single amino acid residue. This result suggests that binding properties alone are not sufficient to explain the transfection potential of the peptides. These results also suggest that the LID vector complex system may be retargeted to other specific peptides described herein and may be useful for targeted gene delivery to epithelial cells in vivo or in vitro.

Example 2

Example 2 is a similar series of experiment to Example 1, with relatively minor changes in a number of conditions.
Cell Lines The human airway epithelial cell line (HAEo−) was maintained in Eagle's minimal essential medium (MEM) HEPES modification (Sigma, Poole) containing 10% foetal calf serum (FCS), penicillin and streptomycin, and L-glutamine. The mouse fibroblast cell line 3T3 and the human neuroblastoma cell line IMR32 were grown in Dulbecco's MEM with Glutamax-1, without sodium pyruvate, with 4500 mg/L glucose, with pyridoxine (Gibco BRL) with 10% FCS, penicillin and streptomycin added. Neuro-2A cells were maintained in Dulbecco's MEM with Glutamax-1 (Gibco BRL) with 10% FCS, sodium pyruvate, penicillin and streptomycin and non-essential amino acids.
Panning Cells in Monolayer HAEo− cells were grown to confluence in 24 well plates. Cells were washed twice in TBS before blocking cells with 2 mls 2% Marvel, 5% BSA-TBS per well for 30 mins at 4° C. The blocker was removed and $2 \times 10^{11}$ phage were added in 1 ml of 2% Marvel, 5% BSA-TBS. The phage were allowed to bind for 2 hours shaking at 4° C. before washing five times with 2% BSA-TBS for 5 mins shaking at 4° C., followed by another five washes with 2% BSA-TBS for a few seconds only. Phage were eluted by the addition of 400 l 76 mM citrate buffer pH 2.5 to the wells for 10 mins shaking at 4° C. The eluate was removed and the remaining cells were lysed with 1 ml 30 mM Tris pH 8.0, 1 mM EDTA for 1 hour on ice. The cells were scraped from the plate, the eluate transferred to an eppendorf, and vortexed briefly. This eluate was saved as the cell-associated fraction. The phage from this elution were titrated as plaque forming units (PFU) as described in the literature supplied with the library by NEB, before amplification of the phage in E. coli ER2738 cells as described in the literature. For the second round of panning, $2 \times 10^{11}$ of the amplified phage from the previous round was used as the input phage. However, in order to reduce the number of plastic and blocking molecule-binding phage isolated, four preselection steps of adding the phage to a blocked well with no cells for 30 mins at 4° C. was carried out before adding the phage to the HAEo− cells. The stringency of washing as also increased in both the second and third rounds by the addition of a 10 min wash at 4° C. using 1 ml 76 mM citrate buffer pH3.5. For the third round, $2 \times 10^{11}$ amplified phage from the second round was preselected in 5 blocked wells containing no cells for 30 mins each, followed by 1 well for 1 hour at 4° C. Phage binding and elution was as described for the second round. Following titration of the third round eluate, single well isolated plaques were picked, amplified and purified for sequencing and clone binding characterisation by whole cell ELISA.
Phage Sequencing The phage were purified from small scale PEG preps (see suppliers methods) and single stranded phage DNA was prepared for sequencing using the method described in Phage display of Peptides and Proteins Edited by Brian K. Kay, Jill Winter and John McCafferty. Briefly, the protein coat was removed from the sample by phenol chloroform extraction, and the DNA pelleted by ethanol precipitation. Trace salt was washed from the pellet with ice cold 70% ethanol before resuspending the DNA in TE.

Between 50 and 100 ng purified DNA was used in a Big Dye terminator cycle sequencing reaction (ABI) using the −96 primer supplied with the library and purified for loading by ethanol precipitation as described in Big Dye kit instructions. The samples were run on an ABI 377 sequencer and the results analysed using the Vector NTI program.
Whole Cell ELISA Approx. $8 \times 10^4$ HAE cells in 100 ml HBSS were added to each well of a 96 well plate and incubated at 37° C. until cells had adhered. The cells were washed gently in HBSS before blocking by the addition of 0.5% BSA in HBSS for 30 mins. $1 \times 10^{10}$ phage particles in blocker were added to each well and allowed to bind at room temperature for 40 mins. Unbound phage were removed by washing twice with HBSS, and bound phage were fixed to the cells by incubation in 3.7% paraformaldehyde for 10 mins. Cells were washed in PBS and incubated in blocking buffer for 45 mins, followed by three washes in PBS. Bound phage were detected by the addition of HRP-conjugated anti-M13 antibody diluted 1:5000 in blocking buffer for 1 hour, before washing three times in PBS, developing the ELISA with ABTS solution, and reading the absorbance at 405 nm.

Peptide Synthesis

The [K]16—forms of the cyclised peptides (as shown in Table 6) were synthesised by standard solid phase synthesis by Alta Biosciences, Birmingham, and the Department of Chemistry, UCL.

TABLE 6

| Phage peptide | SEQ.ID. | Peptide name | Peptide synthesised | SEQ.ID. |
|---|---|---|---|---|
| LPHKSMP | 5 | P | $[K]_{16}$-GACLPHKSMPCG | 13 |
| LQHKSMP | 4 | Q | $[K]_{16}$-GACLQHKSMPCG | 12 |
| YGLPHKF | 19 | Y | $[K]_{16}$-GACYGLPHKFCG | 44 |
| SERSMNF | 7 | E | $[K]_{16}$-GACSERSMNFCG | 27 |
| VKSMVTH | 6 | V | $[K]_{16}$-GACVKSMVTHCG | 28 |
| PSGAARA | 3 | S | $[K]_{16}$-GACPSGAARACG | 29 |
| YKHPGFL | 21 | S/YS | $[K]_{16}$-GACYKHPGFLCG | 30 |
| NSFMESR | 22 | ES | $[K]_{16}$-GACNSFMESRCG | 31 |
| ASSARPA | 23 | OS | $[K]_{16}$-GACAGSARPACG | 32 |
| PLSHQMK | 24 | QS | $[K]_{16}$-GACPLSHQMKCG | 33 |
| HPPMSKL | 25 | PS | $[K]_{16}$-GACHPPMSKLCG | 34 |
| RRETEWA | 26 | 6 | $[K]_{16}$-GACRRETEWACG | 35 |

For the avoidance of doubt, all of the sequences in Table 5 form part of the present invention.

Transfections
Lipopolyplex Formation

Complexes were allowed to form electrostatically in a tube by adding the following components in the following order. 50 μl of Lipofectin (Life Technologies Ltd) diluted to a concentration of 30 μg/ml in OptiMEM, followed by 70 μl peptide (at varying concentrations in OptiMEM for optimisation of the peptide:DNA charge ratio in the complex), with 50 μl of the luciferase reporter plasmid pCILuc at a concentration of 40 ug/ml in Optimem added finally. The complex was mixed by pipetting briefly before diluting in Optimem to a final volume of 1.57 mls.

Transfection

The media was removed from subconfluent HAEo− cells plated at $2 \times 10^4$ cells/well overnight in 96 well plates and 200 μl of complex (approx. 0.25 μg of plasmid DNA) added to each well, leaving minimal time between preparing the complex and adding to the cells. All transfections were carried out in 6 wells each. The cells were incubated with the complexes for 4 hours before replacing with normal media for 48 hours, after which reporter gene expression was analysed by luciferase assay (Promega).

Luciferase Assay

The cells were rinsed twice with PBS before the addition of 100 μl of reporter lysis buffer (Promega, diluted 1 in 5 in dH$_2$O) to the cells for 20 mins at 4° C. before freeze-thawing. 20 μl of the lysate was transferred to a white plate and the luciferase was measured by a Lucy1 luminometer following the addition of 100 μl of reagent.

The protein present in each transfection well was calculated using the Bio-Rad protein assay reagent (based on the Bradford assay), adding 20 μl from the luciferase test to 200 μl of the reagent diluted 1 in 5, incubating for 10 mins at room temperature and reading the absorbance at 590 nm. The total protein present per well was calculated from comparison with a range of BSA standards.

Figure 4:
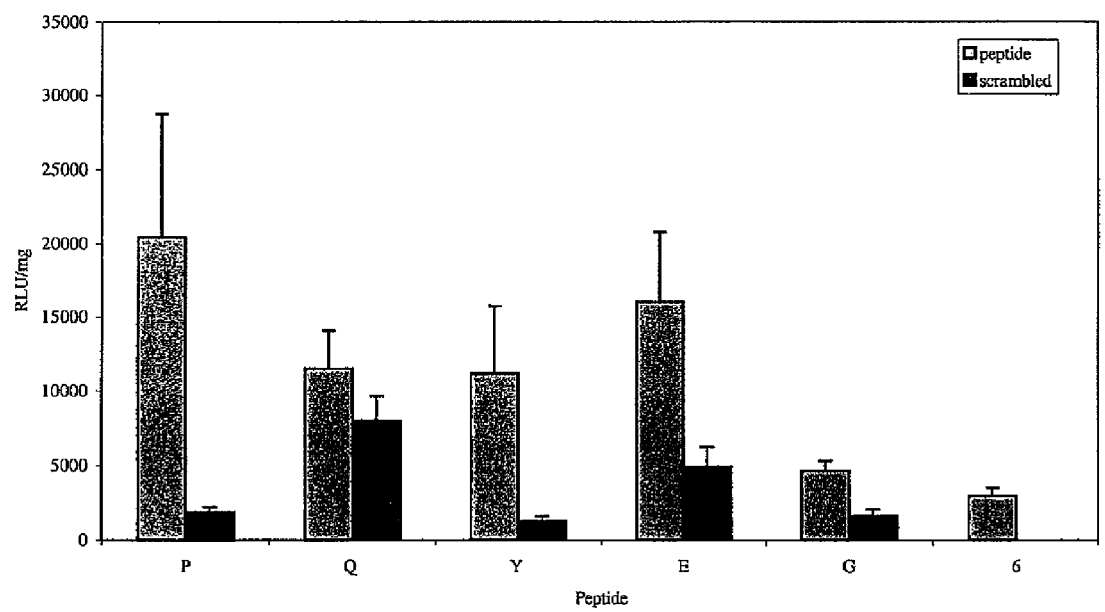
FIG. 4 shows the relative efficiency of transfection of HAE cells achieved by transfection complexes according to the invention and scrambled control peptides.

The results of the transfection experiments are shown in FIG. 4. Transfection of HAEo− cells with phage derived peptides and their scrambled controls was carried out with a range of peptide:DNA charge ratios including 1.5:1, 3:1 and 7:1. The ratio giving the highest transfection efficiency (determined as RLU/mg) for each peptide is shown in the figure. Controls include cells with no transfection complexes added (OptiMEM only) and peptide 6, an integrin binding peptide. Each result is the mean of 6 values and error bars represent the standard deviation about the mean.

Example 3

The transfection experiments described above were repeated using Neuro-2A cells, IMR32 cells, rabbit adventitial fibroblast cells and 3T3 cells. For analysis of transfections of those cell lines, cells were plated to subconfluence overnight before transfecting in the same manner as above, analysing reporter gene expression after 24 hours. The results are shown in FIGS. 5 to 8.

Figure 5:
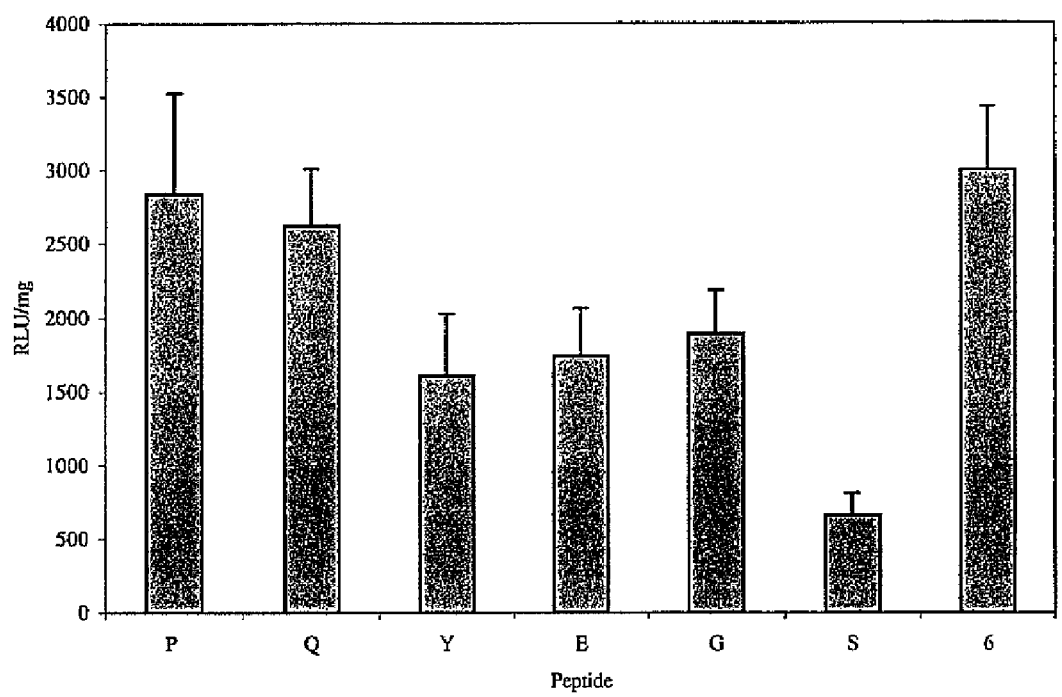
FIG. 5 shows the relative efficiency of transfection of Neuro-2A cells achieved by transfection complexes according to the invention and a control peptide, peptide 6.

Transfection of Neuro-2A cells with phage-derived peptides was carried out with a range of peptide:DNA charge ratios including 1.5:1, 3:1 and 7:1. The ratio giving the highest transfection efficiency (determined as RLU/mg) for each peptide is shown in FIG. 5. Controls included cells with no transfection complexes added (OptiMEM only) peptide 6, an integrin binding peptide, and peptide S, the scrambled version of peptide Y. Each result is the mean of 6 values and error bars represent the standard deviation about the mean.

Figure 6:
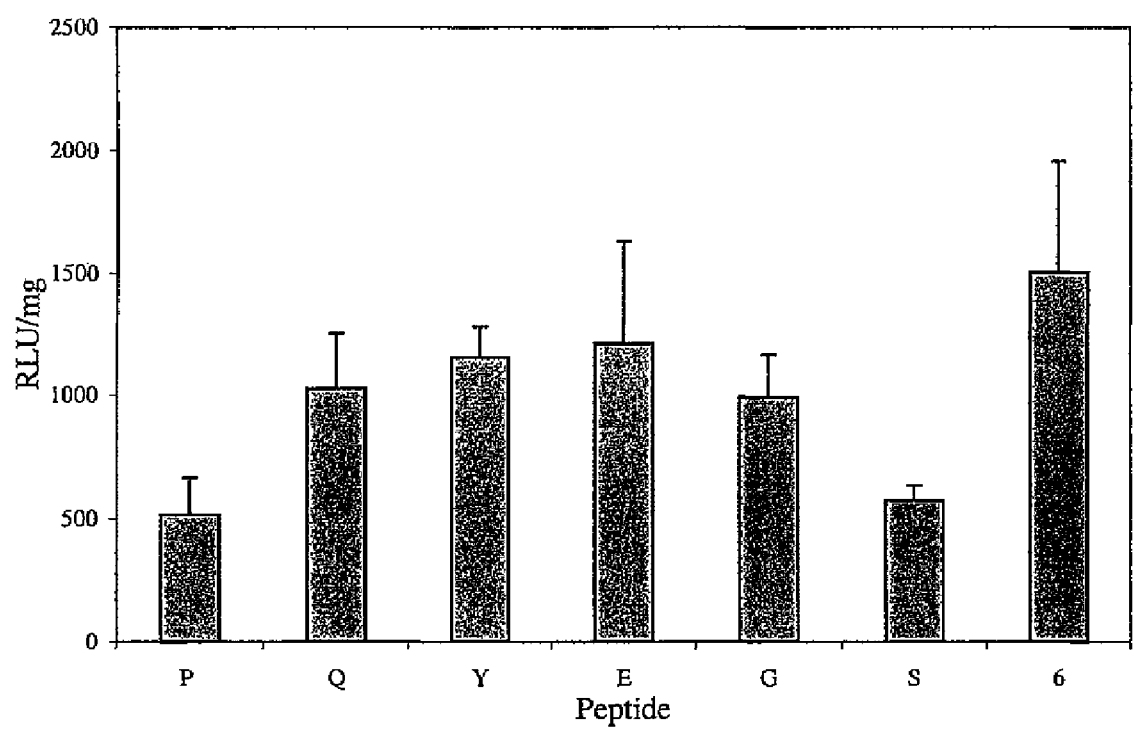
FIG. 6 shows the relative efficiency of transfection of IMR32 cells achieved by transfection complexes according to the invention and a control peptide, peptide 6.

Transfection of IMR32 cells with phage-derived peptides was carried out with a range of peptide:DNA charge ratios including 1.5:1, 3:1 and 7:1. The ratio giving the highest transfection efficiency (determined as RLU/mg) for each peptide is shown in FIG. 6. Controls include cells with no transfection complexes added (OptiMEM only) peptide 6, an integrin binding peptide, and peptide S, the scrambled version of peptide Y. Each result is the mean of 6 values and error bars represent the standard deviation about the mean.

Transfection of rabbit adventitial fibroblast cells with phage-derived peptides was carried out with a range of peptide:DNA charge ratios including 1.5:1, 3:1 and 7:1. The ratio giving the highest transfection efficiency (determined as RLU/mg) for each peptide is shown FIG. 7. Controls include cells with no transfection complexes added (OptiMEM only) peptide 6, an integrin binding peptide, and peptide S, the scrambled version of peptide Y. Each result is the mean of 6 values and error bars represent the standard deviation about the mean.

Figure 8:
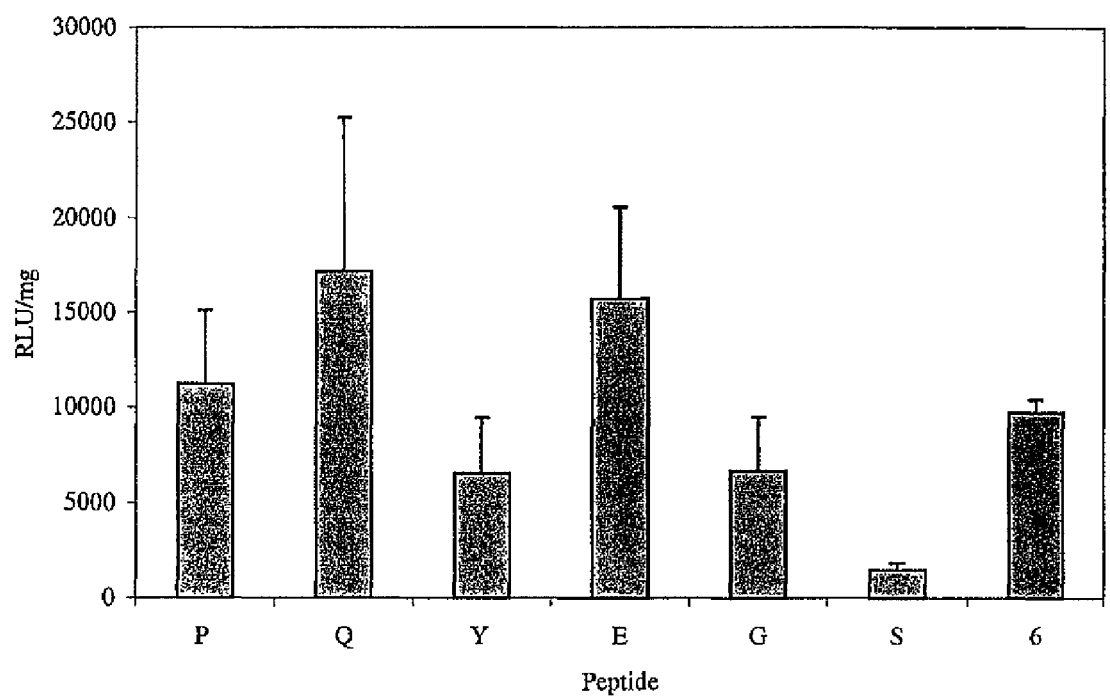
FIG. 8 shows the relative efficiency of transfection of 3T3 cells achieved by transfection complexes according to the invention and a control peptide, peptide 6.

Transfection of 3T3 cells with phage-derived peptides was carried out with a range of peptide:DNA charge ratios including 1.5:1, 3:1 and 7:1. The ratio giving the highest transfection efficiency (determined as RLU/mg) for each peptide is shown in FIG. 8. Controls include cells with no transfection complexes added (OptiMEM only) peptide 6, an integrin binding peptide, and peptide S, the scrambled version of peptide Y. Each result is the mean of 6 values and error bars represent the standard deviation about the mean.

Figure 7:
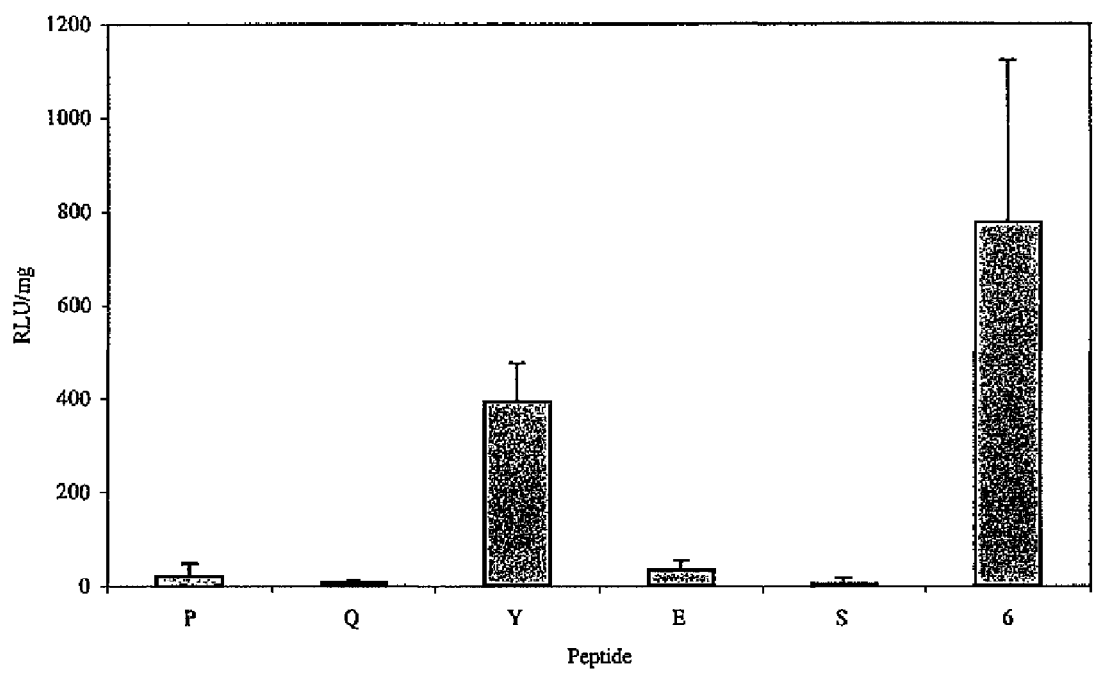
FIG. 7 shows the relative efficiency of transfection of rabbit adventitial cells achieved by transfection complexes according to the invention and a control peptide, peptide 6.

It is seen in FIGS. 5, 6 and 7 that transfection of Neuro-2A cells, IMR32 cells, rabbit adventitial fibroblast cells with the peptides was of similar efficiency or lower than transfection with peptide 6. Only in 3T3 cells (FIG. 8) was the transfection efficiency above that seen with peptide 6, with peptides Q and E showing efficiencies of approximately 1.5 times that seen with peptide 6. All transfections showed efficiencies above that of the scrambled peptide. These results may suggest that the molecules bound by the peptide are present on other cell types and in other species but maybe in altered forms or at different densities compared to HAEo− cells.

REFERENCES

1. Wu G Y, Wu C H. Receptor-mediated in vitro gene transformation by a soluble DNA carrier system. J Biological Chemistry 1987; 262(10):4429-4432.
2. Wagner E, Cotten M, Mechtler K, Kirlappos H, Birnstiel M L. DNA-binding transferrin conjugates as functional gene-delivery agents: Synthesis by linkage of polylysine or ethidium bromide to the transferrin carbohydrate moiety. Bioconjugate Chemistry 1991; 2:226-231.
3. Cotten M, Lange. Transferrin-polycation-mediated introduction of DNA into human leukemic cells: Stimulation by agents that affect the survival of transfected DNA or modulate transferrin receptor levels. PNAS 1990; 87:4033-4037.
4. Ferkol T, Perales J C, Eckman E, Kaetzel C S, Hanson R W, Davis P B. Gene transfer into the airway epithelium of animals by targeting the polymeric immunoglobulin receptor. J Clinical Investigation 1995; 95:493-502.
5. Curiel D T, Agarwal S, Wagner E, Cotten M. Adenovirus enhancement of transferrin-polylysine-mediated gene delivery. PNAS 1991; 88:8850-8854.
6. Fernandez M A, Muno-Fernandez M A, Fresno M. Involvement of β1 integrins in the binding and entry of *Trypanosoma cruzi* into human macrophages. European J of Immunology 1993; 23:552-557.
7. Wickham T J, Filardo E J, Cheresh D A, Nemerow G R. Integrin αvβ5 selectively promotes adenovirus mediated cell membrane permeabilization. J Cell Biology 1994; 127(1):257-264.
8. Bergelson J M, Shepley M P, Chan B M C, Hemler M E, Finberg R W. identification of the integrin VLA-2 as a receptor for echovirus 1. Science 1992; 255:1718-1720.
9. Logan D, Abu-Ghazaleh R, Blakemore W, et al. Structure of a major immunogenic site on foot-and-mouth disease virus. Nature 1993; 362:566-568.
10. Isberg R R. Discrimination between intracellular uptake and surface adhesion of bacterial pathogens. Science 1991; 252:934-938.
11. Almeida E A C, Huovilla A-P J, Sutherland A E, et al. Mouse egg integrin α6β1 functions as a sperm receptor. Cell 1995; 81:1095-1104.
12. Clements J M, Newham P, Shepherd M, et al. Identification of a key integrin-binding sequence in VCAM-1 homologous to the LDV active site in fibronectin. J Cell Science 1994; 107:2127-2135.
13. Lu X, Deadman J J, Williams J A, Kakkar V V, Rahman S. Synthetic RGD peptides derived from the adhesive domains of snake-venom proteins: evaluation as inhibitors of platelet aggregation. Biochemistry J 1993; 296:21-24.
14. Koivunen E, Wang B, Ruoslahti E. Phage libraries displaying cyclic peptides with different ring sizes: ligand specificities of the RGD-directed integrins. Biol/Technology 1995; 13:265-270.
15. Koivunen E, Gay D A, Ruoslahti E. Selection of peptides binding to the α5β1 integrin from phage display library. J Biological Chemistry 1993; 268(27):20205-20210.
16. Koivunen E, Wang B, Ruoslahti E. Isolation of a highly specific ligand for the α5β1 integrin from a phage display library. J Cell Biology 1994; 124(3):373-380.
17. O'Neil K T, Hoess R H, Jackson A, Ramachandran N S, Mousa A, DeGrado W F. Identification of novel peptide antagonists for GPIIb/IIIa from a conformationally constrained phage peptide library. Proteins 1992; 14:509-515.
18. Healy J M, Murayama O, Maeda T, Yoshino K, Sekiguchi K, Kikuchi M. Peptide ligands for integrin alpha v beta 3 selected from random phage display libraries. Biochemistry 1995; 34:3948-3955.
19. Pasqualani R, Koivunen E, Ruoslahti E. A peptide isolated from phage display libraries is a structural and functional mimic of an RGD-binding site on integrins. J Cell Biology 1995; 130:1189-1196.
20. Hart S L, Knight A M, Harbottle R P, et al. Cell binding and internalization by filamentous phage displaying a cyclic Arg-Gly-Asp-containing peptide. J Biological Chemistry 1994; 269:12468-12474.
21. Hart S L, Harbottle R P, Cooper R, Miller A, Williamson R, Coutelle C. Gene delivery and expression mediated by an integrin-binding peptide. Gen Therapy 1995; 2:552-554.
22. Wolfert M A, Seymour L W. Atomic force microscopic analysis of the influence of the molecular weight of poly (L)lysine on the size of polyelectrolyte complexes formed with DNA. Gene Therapy 1996; 3:269-273.
23. Hart S L, Collins L, Gustaffson K, Fabre J W. Integrin mediated transfection with peptides containing arginine-glycine-aspartic acid domains. In press 1997.
24. Farhood H, Sebina A, Huang L. The role of dioleyl phosphatidylethanolamine (DOPE) in cationic liposome mediated gene transfer. Biochem Biophys Acta 1995; 1235: 289-295.
25. Anderson R, MacDonald I, Corbett T, Hacking G, Lowdell M W and Prentice H G. Human Gene Therapy 1997; 8:1125-1135.
26. Blank R S, Thompson M M and Owens G K. Journal of Cell Biology 1988; 107:299.
27. Bettinger, T., Remy, J. S. and Erbacher, P. (1999) Size reduction of galactosylated PEI/DNA complexes improves lectin-mediated gene transfer into hepatocytes. *Bioconjug Chem*, 10, 558-61.
28. Brunner, S., Sauer, T., Carotta, S., Cotten, M., Saltik, M. and Wagner, E. (2000) Cell cycle dependence of gene transfer by lipoplex, polyplex and recombinant adenovirus. *Gene Ther*, 7, 401-7.
29. Feero, W. G., Li, S., Rosenblatt, J. D., Sirianni, N., Morgan, J. E., Partridge, T. A., Huang, L. and Hoffman, E. P. (1997) Selection and use of ligands for receptor-mediated gene delivery to myogenic cells. *Gene Ther*, 4, 664-74.
30. Aberland, A., Knaus, T., Zaitsev, S. V., Stahn, R., Mistry, A. R., Coutelle, C., Haller, H. and Bottger, M. (1999) Calcium ions as efficient cofactor of polycation-mediated gene transfer. *Biochim Biophys Acta*, 1445, 21-30.
31. Han, J., Lim, M. and Yeom, Y. I. (1999) Receptor-mediated gene transfer to cells of hepatic origin by galactosylated albumin-polylysine complexes. *Biol Pharm Bull*, 22, 836-40.
32. Park, J. M., Yang, X., Park, J. J., Press, O. W. and Press, M. F. (1999) Assessment of novel anti-p185HER-2 monoclonal antibodies for internalization-dependent therapies. *Hybridoma*, 18, 487-95.
33. Phillips, S. C. (1995) Receptor-mediated DNA delivery approaches to human gene therapy. *Biologicals*, 23, 13-6.
34. Reddy, J. A., Dean, D., Kennedy, M. D. and Low, P. S. (1999) Optimization of folate-conjugated liposomal vectors for folate receptor-mediated gene therapy. *J Pharm Sci*, 88, 1112-8.

35. Reddy, J. A. and Low, P. S. (2000) Enhanced folate receptor mediated gene therapy using a novel pH– sensitive lipid formulation. *J Controlled Release,* 64, 27-37.
36. Tseng, W. C., Haselton, F. R. and Giorgio, T. D. (1999) Mitosis enhances transgene expression of plasmid delivered by cationic liposomes. *Biochim Biophys Acta,* 1445, 53-64.
38. Uherek, C., Fominaya, J. and Wels, W. (1998) A modular DNA carrier protein based on the structure of diphtheria toxin mediates target cell-specific gene delivery. *J Biol Chem,* 273, 8835-41.
39. Wang, G., Davidson, B. L., Melchert, P., Slepushkin, V. A., van Es, H. H., Bodner, M., Jolly, D. J. and McCray, P. B., Jr. (1998) Influence of cell polarity on retrovirus-mediated gene transfer to differentiated human airway epithelia. *J Virol,* 72, 9818-26.
40. Wang, G., Zabner, J., Deering, C., Launspach, J., Shao, J., Bodner, M., Jolly, D. J., Davidson, B. L. and McCray, P. (2000) Increasing epithelial junction permeability enhances gene transfer to airway epithelia In vivo. *Am J Respir Cell Mol Biol,* 22, 129-38.
41. Wilke, M., Fortunati, E., van den Broek, M., Hoogeveen, A. T. and Scholte, B. J. (1996) Efficacy of a peptide-based gene delivery system depends on mitotic activity. *Gene Ther,* 3, 1133-42.
42. Wu, G. Y., Wilson, J. M., Shalaby, F., Grossman, M., Shafritz, D. A. and Wu, C. H. (1991) Receptor-mediated gene delivery in vivo. Partial correction of genetic analbuminemia in Nagase rats. *J Biol Chem,* 266, 14338-42.
43. Yano, L., Shimura, M., Taniguchi, M., Hayashi, Y., Suzuki, T., Hatake, K., Takaku, F. and Ishizaka, Y. (2000) Improved gene transfer to neuroblastoma cells by a monoclonal antibody targeting RET, a receptor tyrosine kinase [In Process Citation]. *Hum Gene Ther,* 11, 995-1004.
44. Zhang, F., Andreassen, P., Fender, P., Geissler, E., Hernandez, J. F. and Chroboczek, J. (1999) A transfecting peptide derived from adenovirus fiber protein. *Gene Ther,* 6, 171-81.

The invention claimed is:

1. An isolated peptide of 7 to 100 amino acids comprising an amino acid sequence including KSM, wherein said amino acid sequence is selected from LX$^5$HKSMP [SEQ ID NO.: 18], in which X$^5$ is P or Q, and VKSMVTH [SEQ ID NO.:6], and wherein said amino acid sequence binds to a cell surface receptor.

2. The isolated peptide according to claim 1, wherein the amino acid sequence is LQHKSMP [SEQ ID NO:4] or LPHKSMP [SEQ ID NO:5].

3. The isolated peptide according to claim 1, consisting of 7 to 20 amino acids.

4. The isolated peptide according to claim 1, consisting of 7 to 12 amino acids.

5. The isolated peptide according to claim 1, wherein the peptide is comprised within a cyclic region of amino acids.

6. The isolated peptide according to claim 5, wherein the peptide comprises two or more cysteine residues capable of forming one or more disulphide bond(s).

7. The isolated peptide according to claim 1, wherein the peptide is linked to a polycationic nucleic acid-binding component.

8. The isolated peptide according to claim 7, wherein the polycationic nucleic acid-binding component is selected from polyethylenimine and an oligo-lysine molecule consisting of from 5 to 25 lysine moieties.

9. The isolated peptide according to claim 7, wherein the peptide is linked to the polycationic nucleic acid-binding component via a spacer element.

10. The isolated peptide according to claim 9, wherein the spacer element is GG or GA or is longer and/or more hydrophobic than the dipeptide spacers GG (glycine-glycine) and GA (glycine-alanine).

11. A peptide derivative of formula A-B-C wherein
A is a polycationic nucleic acid-binding component,
B is a spacer element, and
C is a peptide according to claim 1.

12. A mixture comprising a cell surface receptor-binding component, a polycationic nucleic acid-binding component, and optimally a lipid component, the cell surface receptor-binding component being a peptide as defined in claim 1.

13. The mixture according to claim 12, wherein said cell surface receptor-binding component is a peptide of 7 to 20 amino acids comprising an amino acid sequence selected from the group consisting of: VKSMVTH [SEQ ID NO.:6], LQHKSMP [SEQ ID NO:4] or LPHKSMP [SEQ ID NO:5], and cyclic peptides thereof.

14. The mixture according to claim 13, wherein the polycationic nucleic acid-binding component is comprised of 3 to 100 cationic monomers and is selected from the group consisting of oligolysine, polyethyleneimine, and combinations thereof.

15. The mixture according to claim 13 or claim 14, wherein the lipid component is selected from the group consisting of dioleyl phosphatidyl-ethanolamine (DOPE), N-[1-(2,3-dioleyloxy)propyl]-N,N,N-trimethylammonium chloride (DOTMA), or combinations thereof.

16. The mixture according to claim 14, which comprises an equimolar mixture of DOPE and DOTMA as the lipid component, and [K]$_{16}$ as the polycationic component nucleic acid-binding component.

17. A process for producing a nucleic acid-containing transfection vector complex, which comprises incorporating a nucleic acid with a mixture according to claim 12.

18. A kit that comprises
(i) nucleic acid,
(ii) optionally, a lipid component,
(iii) a polycationic nucleic acid-binding component, and (iv) a cell surface receptor binding component, comprising a peptide as defined in claim 1.

19. A non-viral transfection complex comprising:
(i) a nucleic acid,
(ii) optionally, a lipid component,
(iii) a polycationic nucleic acid-binding component, and
(iv) a cell surface receptor binding component, comprising a peptide as defined in claim 1.

20. A method of transfecting a cell with a nucleic acid, which comprises contacting the cell in vitro or in vivo with a complex according to claim 19.

21. A pharmaceutical composition which comprises a complex according to claim 19, in admixture or conjunction with a pharmaceutically suitable carrier.

22. A method for expressing a gene in a human or in a non-human animal with a defect and/or a deficiency in a gene, which comprises administering a complex as defined in claim 19 to the human or to the non-human animal.

23. A method for inducing an immune response in a human or a non-human animal, which comprises administering a complex as defined in claim 19 to the human or to the non-human animal.

24. A method of inhibiting the expression of a gene, which comprises administering a complex as defined in claim 19 to a human or to a non-human animal, wherein the expression of the gene is inhibited by the expression of an antisense nucleic acid.

* * * * *